(12) United States Patent
Verma et al.

(10) Patent No.: US 10,321,247 B2
(45) Date of Patent: Jun. 11, 2019

(54) EXTERNAL COMPONENT WITH INDUCTANCE AND MECHANICAL VIBRATORY FUNCTIONALITY

(71) Applicant: Cochlear Limited, Macquarie University, NSW OT (AU)

(72) Inventors: Rishubh Verma, Mechelen (BE); Jan Vermeiren, Mechelen (BE); Kristof Buytaert, Mechelen (BE)

(73) Assignee: Cochlear Limited, Macquarie University, NSW (AU)

( * ) Notice: Subject to any disclaimer, the term of this patent is extended or adjusted under 35 U.S.C. 154(b) by 302 days.

(21) Appl. No.: 15/163,947

(22) Filed: May 25, 2016

(65) Prior Publication Data

US 2017/0156010 A1 Jun. 1, 2017

Related U.S. Application Data

(60) Provisional application No. 62/260,386, filed on Nov. 27, 2015.

(51) Int. Cl.
*H04R 25/00* (2006.01)
*A61N 1/36* (2006.01)
*H04B 1/3827* (2015.01)
*A61N 1/372* (2006.01)

(52) U.S. Cl.
CPC ....... *H04R 25/606* (2013.01); *A61N 1/36036* (2017.08); *A61N 1/37211* (2013.01); *H04R 25/554* (2013.01); *H04R 2225/51* (2013.01); *H04R 2225/67* (2013.01); *H04R 2460/13* (2013.01)

(58) Field of Classification Search
CPC ................ H04R 25/606; H04R 25/554; H04R 2225/67; H04R 2225/51; H04R 2460/13; A61N 1/36036
See application file for complete search history.

(56) References Cited

U.S. PATENT DOCUMENTS

| 3,712,962 A | 1/1973 | Epley |
| 3,870,832 A | 3/1975 | Fredrickson |
| 3,882,285 A | 5/1975 | Nunley et al. |
| 4,352,960 A | 10/1982 | Dormer et al. |

(Continued)

FOREIGN PATENT DOCUMENTS

| DE | 19618964 A1 | 11/1997 |
| DE | 10047388 C1 | 1/2002 |

(Continued)

OTHER PUBLICATIONS

European Application No. 01118055, Search Report dated Feb. 22, 2005.

(Continued)

*Primary Examiner* — Christine H Matthews
*Assistant Examiner* — Joshua Daryl D Lannu
(74) *Attorney, Agent, or Firm* — Pilloff & Passino LLP; Martin J. Cosenza

(57) ABSTRACT

A device including an inductive radio frequency communication coil and a platform apparatus configured to be secured or coupled to an actuator such that the actuator can induce vibration in the skull inducing hearing percepts, and the RF coil can deliver communication allowing an implantable stimulator to also induce hearing percepts.

33 Claims, 13 Drawing Sheets

(56) References Cited

U.S. PATENT DOCUMENTS

| | | |
|---|---|---|
| 4,498,461 A | 2/1985 | Hakansson |
| 4,581,491 A | 4/1986 | Boothroyd |
| 4,612,915 A | 9/1986 | Hough et al. |
| 4,669,688 A | 6/1987 | Itoh et al. |
| D294,295 S | 2/1988 | Brånemark |
| 4,729,366 A | 3/1988 | Schaefer |
| 4,850,962 A | 7/1989 | Schaefer |
| 4,957,478 A | 9/1990 | Maniglia |
| 4,958,791 A | 9/1990 | Nakamura |
| 4,979,087 A | 12/1990 | Sellwood et al. |
| 5,015,224 A | 5/1991 | Maniglia |
| 5,015,225 A | 5/1991 | Hough et al. |
| 5,079,802 A | 1/1992 | Blase et al. |
| 5,176,620 A | 1/1993 | Gilman |
| 5,217,011 A | 6/1993 | Bisch |
| 5,277,694 A | 1/1994 | Leysieffer et al. |
| 5,279,292 A | 1/1994 | Baumann et al. |
| 5,360,388 A | 11/1994 | Spindel et al. |
| 5,411,467 A | 5/1995 | Hortmann et al. |
| 5,554,096 A | 9/1996 | Ball |
| 5,624,379 A | 4/1997 | Ganz et al. |
| 5,707,338 A | 1/1998 | Adams et al. |
| 5,735,790 A | 4/1998 | Hakansson et al. |
| 5,788,711 A | 8/1998 | Lehner et al. |
| 5,814,095 A | 9/1998 | Muller et al. |
| 5,935,170 A | 8/1999 | Hakansson et al. |
| 5,941,814 A | 8/1999 | Lehner et al. |
| 5,984,859 A | 11/1999 | Lesinski |
| 5,999,632 A | 12/1999 | Leysieffer et al. |
| 6,030,333 A | 2/2000 | Sioshansi et al. |
| 6,051,008 A | 4/2000 | Saadat et al. |
| 6,077,215 A | 6/2000 | Leysieffer |
| 6,123,660 A | 9/2000 | Leysieffer |
| 6,139,488 A | 10/2000 | Ball |
| 6,162,169 A | 12/2000 | Leysieffer |
| 6,171,229 B1 | 1/2001 | Kroll et al. |
| 6,277,148 B1 | 8/2001 | Dormer |
| 6,293,903 B1 | 9/2001 | Kasic, II et al. |
| 6,325,755 B1 | 12/2001 | Bushek et al. |
| 6,473,651 B1 | 10/2002 | Kuzma et al. |
| 6,482,144 B1 | 11/2002 | Muller |
| 6,491,622 B1 | 12/2002 | Kasic, II et al. |
| 6,517,476 B1 | 2/2003 | Bedoya et al. |
| 6,537,199 B1 | 3/2003 | Muller et al. |
| 6,579,317 B2 | 6/2003 | Kurz |
| 6,611,718 B2 | 8/2003 | Zilberman et al. |
| 6,705,985 B2 | 3/2004 | Easter et al. |
| 6,940,989 B1 | 9/2005 | Shennib et al. |
| 6,945,999 B2 | 9/2005 | Schneider et al. |
| 7,153,257 B2 | 12/2006 | Schneider et al. |
| 7,166,069 B2 | 1/2007 | Schneider et al. |
| 7,186,211 B2 | 3/2007 | Schneider et al. |
| 7,204,800 B2 | 4/2007 | Easter et al. |
| 7,226,406 B2 | 6/2007 | Muller et al. |
| 7,278,963 B2 | 10/2007 | Schneider et al. |
| 7,346,397 B2 | 3/2008 | Money et al. |
| 7,468,028 B2 | 12/2008 | Schneider et al. |
| 7,582,052 B2 | 9/2009 | Waldmann |
| 7,722,525 B2 | 5/2010 | Andrews |
| 8,105,229 B2 | 1/2012 | Muller et al. |
| 8,244,365 B2 | 8/2012 | van Dijk et al. |
| 2001/0031996 A1 | 10/2001 | Leysieffer |
| 2002/0038072 A1 | 3/2002 | Muller et al. |
| 2003/0055311 A1 | 3/2003 | Neukermans et al. |
| 2004/0133250 A1 | 7/2004 | Ball et al. |
| 2005/0020873 A1 | 1/2005 | Berrang et al. |
| 2005/0225180 A1 | 10/2005 | Schneider et al. |
| 2005/0249366 A1 | 11/2005 | Westerkull |
| 2006/0161255 A1 | 7/2006 | Zarowski et al. |
| 2006/0233409 A1 | 10/2006 | Weidner |
| 2007/0055092 A1 | 3/2007 | Easter et al. |
| 2008/0004486 A1 | 1/2008 | Andrews et al. |
| 2008/0051623 A1 | 2/2008 | Schneider et al. |
| 2009/0023976 A1 | 1/2009 | Cho et al. |
| 2009/0024183 A1 | 1/2009 | Fitchmun |
| 2009/0054980 A1 | 2/2009 | Ludlow |
| 2009/0124849 A1 | 5/2009 | Pergola |
| 2009/0149697 A1 | 6/2009 | Steinhardt et al. |
| 2009/0187065 A1 | 7/2009 | Basinger |
| 2009/0306458 A1 | 12/2009 | Parker et al. |
| 2010/0042119 A1 | 2/2010 | Simms et al. |
| 2010/0137941 A1 | 6/2010 | Darley et al. |
| 2010/0324355 A1 | 12/2010 | Spitaels et al. |
| 2012/0059435 A1 | 3/2012 | Daly |
| 2012/0109006 A1 | 5/2012 | James et al. |
| 2012/0136197 A1 | 5/2012 | Van Gerwen |
| 2012/0245406 A1 | 9/2012 | Aghamohammadi |
| 2013/0343585 A1* | 12/2013 | Bennett ............... H04R 25/554 381/315 |
| 2015/0119635 A1 | 4/2015 | Gustafsson et al. |

FOREIGN PATENT DOCUMENTS

| | | |
|---|---|---|
| EP | 0812577 A2 | 12/1997 |
| EP | 1191816 A2 | 3/2002 |
| WO | 98/06235 A1 | 2/1998 |
| WO | 98/06236 A1 | 2/1998 |
| WO | 98/06237 A1 | 2/1998 |
| WO | 98/06238 A1 | 2/1998 |
| WO | 00/48426 A2 | 8/2000 |
| WO | 02/09622 A1 | 2/2002 |
| WO | 2006/058368 A1 | 6/2006 |
| WO | 2007/023164 A1 | 3/2007 |
| WO | 2008/051848 A2 | 5/2008 |
| WO | 2012/073208 A1 | 6/2012 |
| WO | 2015/024581 A1 | 2/2015 |

OTHER PUBLICATIONS

Australian Application No. 2006201582, Examiner's First Report dated Feb. 11, 2008.
Australian Application No. 63611101, Examiner's First Report dated Jul. 14, 2004.
Fredrickson et al., "Ongoing investigations into an implantable Electromagnetic Hearing Aid for Moderate to Severe Sensorineural Hearing Loss", Otolaryngologlc Clinics of North America, vol. 28, No. 1, Feb. 1995, pp. 107-121.
Leysieffer et al., "Ein implantierbarer piezoelektrischer Horgeratewandler fur Innenohrschwerhorige. Teil I: Entwicklung eines Prototypen", HNO, vol. 45, Oct. 1997, pp. 792-800.
Leysieffer , "Ein implantierbarer piezoelektrischer Horgeratewandler fur Innenohrschwerhorige. Teil II: Klinisches Implantat", HNO, vol. 45, Oct. 1997, pp. 801-815.
Leysieffer et al., "Ein volistandig implantierbares Horsystem fur innenohrschwerhorige: TICA LZ 3001 ", HNO, vol. 46, Jun. 1998, pp. 853-863.
Maniglia et al., "Contactless Semi-Implantable Electromagnetic Middle Ear Device for the Treatment of Sensorineural Hearing Loss", Otolaryngologic Clinics of North America, vol. 28, No. 1, Feb. 1995, pp. 121-140.
International Application No. PCT/IB2011/055396, International Search Report dated May 14, 2012.
Suzuki et al., "Implantation of Partially Implantable Middle Ear Implant and the Indication", Karger Basel-Advances in Audiology, vol. 4, 1988, pp. 160-166.
Traynor et al., "The Future is Here: The Otologics Fully Implantable Hearing System", AudiologyOnline, Retrieved on Nov. 19, 2007, Document Available at: http://www.audiologyon line.corn/articles/ i;!f article detail.as12?articleid0001903.
Yanagihara et al., "Efficacy of the Partially Implantable Middle Ear Implant in Middle and Inner Ear Disorders", vol. 4, 1988, pp. 149-159.
Zenner, "Aktive elektronische Horimplantate fur Mittel- und Innenohrschwerhorige—eine neue Ara der Ohrchirurgie Teil I: Grundprinzipien und Nomenklaturvorschlag", HNO, Oct. 1997, pp. 749-757.
Zenner, "Aktive elektronische Horimplantate fur Mittel- und Innenohrschwerhorige—eine neue Ara der Ohrchirurgie Teil II: Gegenwartiger Entwicklungsstand", HNO, Oct. 1997, pp. 758-768.

(56) References Cited

OTHER PUBLICATIONS

Zenner et al., "Aktive elektronische Horimplantate fur Mittel- und Innenohrschwerhorige—eine neue Ara der Ohrchirurgie Teil III: Perspektiven fiir Innenohrschwerhorige", HNO, Oct. 1997, pp. 769-774.

Zenner , "Erste Implantationen eines vollstandig implantierbaren elektronischen Horsystems bei Patienten mit Innenohrschwerhorigkeit", HNO, Oct. 1998, pp. 844-852.

* cited by examiner

EXTERNAL COMPONENT WITH INDUCTANCE AND MECHANICAL VIBRATORY FUNCTIONALITY

CROSS-REFERENCE TO RELATED APPLICATIONS

This application claims priority to Provisional U.S. Patent Application No. 62/260,386, entitled EXTERNAL COMPONENT WITH INDUCTANCE AND MECHANICAL VIBRATORY FUNCTIONALITY, filed on Nov. 27, 2015, naming Jan VERMEIREN of Mechelen, Belgium as an inventor, the entire contents of that application being incorporated herein by reference in its entirety.

BACKGROUND

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. One example of a hearing prosthesis is a cochlear implant.

Conductive hearing loss occurs when the normal mechanical pathways that provide sound to hair cells in the cochlea are impeded, for example, by damage to the ossicular chain or the ear canal. Individuals suffering from conductive hearing loss may retain some form of residual hearing because the hair cells in the cochlea may remain undamaged.

Individuals suffering from hearing loss typically receive an acoustic hearing aid. Conventional hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea, causing motion of the perilymph and stimulation of the auditory nerve. Cases of conductive hearing loss typically are treated by means of bone conduction hearing aids. In contrast to conventional hearing aids, these devices use a mechanical actuator that is coupled to the skull bone to apply the amplified sound.

In contrast to hearing aids, which rely primarily on the principles of air conduction, certain types of hearing prostheses, commonly referred to as cochlear implants, convert a received sound into electrical stimulation. The electrical stimulation is applied to the cochlea, which results in the perception of the received sound.

Many devices, such as medical devices that interface with a recipient, have structural and/or functional features where there is utilitarian value in adjusting such features for an individual recipient. The process by which a device that interfaces with or otherwise is used by the recipient is tailored or customized or otherwise adjusted for the specific needs or specific wants or specific characteristics of the recipient is commonly referred to as fitting. One type of medical device where there is utilitarian value in fitting such to an individual recipient is the above-noted cochlear implant. That said, other types of medical devices, such as other types of hearing prostheses, exist where there is utilitarian value in fitting such to the recipient.

SUMMARY

In accordance with an exemplary embodiment, there is a transcutaneous radio frequency (RF) communication system, comprising an external component including a first RF communication apparatus, a transducer configured to at least one of convert electrical input into mechanical output or mechanical input into electrical output, and a first magnetic apparatus. The communication system further includes an implantable component including a second RF communication apparatus, and a second magnetic apparatus, wherein the system is configured to hold the external component to skin of the recipient via magnetic attraction between the first magnetic and the second magnetic with a force of between and including about 0.75N and about 1.05N when the first magnetic is separated from the second magnetic by about 1 mm to about 10 mm of human skin.

In accordance with another exemplary embodiment, there is a method, comprising evoking a first hearing percept in a recipient via electrical stimulation of a first cochlea thereof based on a transcutaneous transmitted RF signal, and evoking a second hearing percept in the recipient via bone conduction stimulation of the first cochlea based on a transcutaneously transmitted mechanical vibration, wherein the transcutaneously transmitted mechanical vibration and the transcutaneously transmitted RF signal enter the skin of the recipient at least at locations that are proximate one another.

In accordance with another exemplary embodiment, there is a device, comprising an inductive radio frequency (RF) communication coil, and a platform apparatus configured to at least one of be secured to or be coupled to an actuator so as to establish a vibrational path from the actuator to a skin interface portion of the platform apparatus, wherein the coil is proximate the skin interface portion.

In accordance with another exemplary embodiment, there a method, comprising generating RF signals extracutaneously to a recipient and evoking a first hearing percept in the recipient via electrical stimulation based on the RF signals, and generating mechanical vibration signals extracutaneously to the recipient and evoking a second hearing percept in the recipient via the bone conduction based on the mechanical vibrations, wherein the method is executed by limiting the generated vibrations to about 2000 Hz and below.

BRIEF DESCRIPTION OF THE DRAWINGS

Embodiments are described below with reference to the attached drawings, in which.

DETAILED DESCRIPTION

Figure 1:
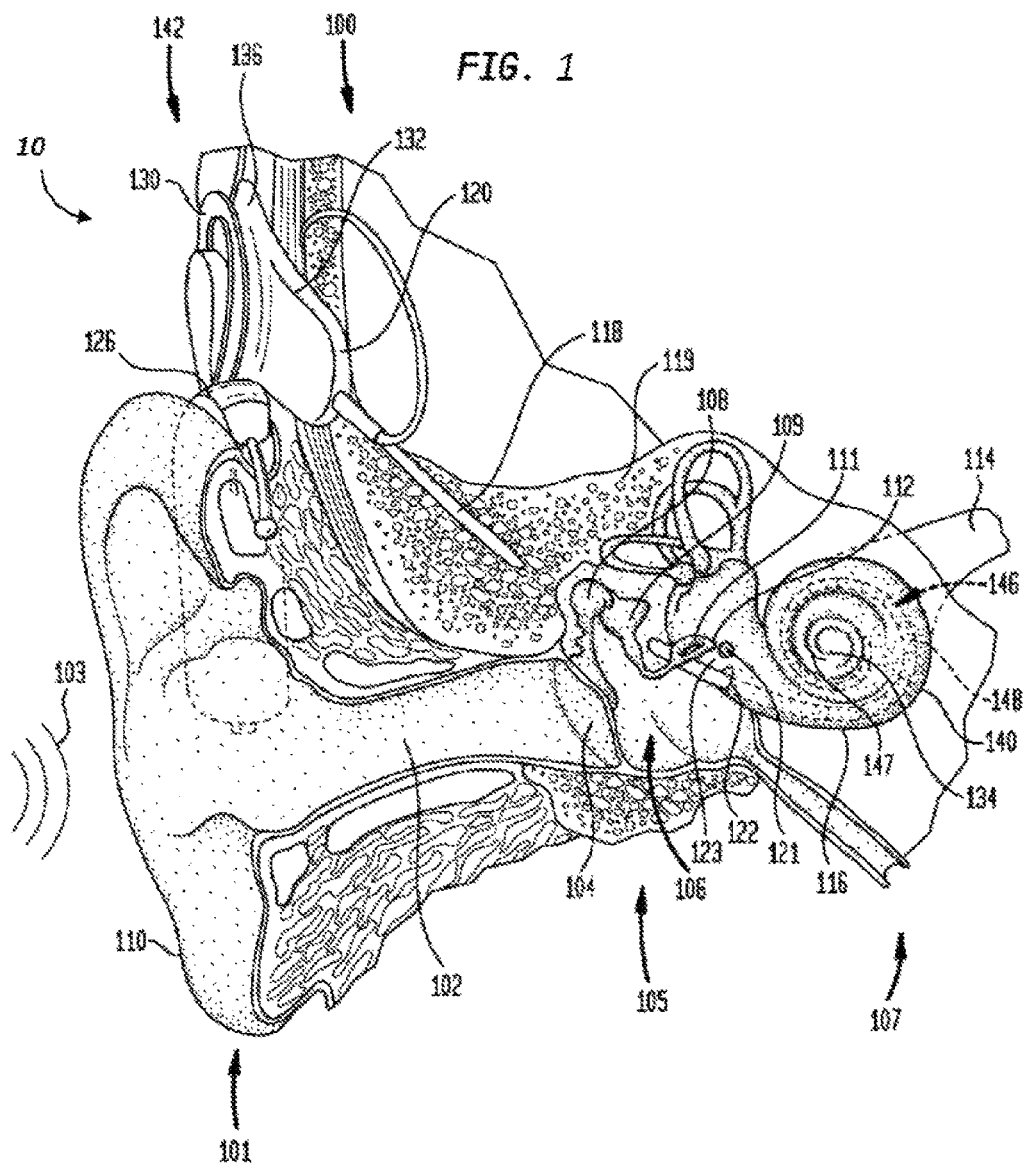
FIG. 1 is a perspective view of an exemplary hearing prosthesis in which at least some of the teachings detailed herein are applicable.

FIG. 1 is a perspective view of a system 10 that includes a cochlear implant, referred to as cochlear implant 100, implanted in a recipient, to which some embodiments detailed herein and/or variations thereof are applicable. The cochlear implant 100 is part of a system 10 that can include external components in some embodiments, as will be detailed below, which external components can include a passive transcutaneous bone conduction device. It is noted that the teachings detailed herein are applicable, in at least some embodiments, to partially implantable and/or totally implantable cochlear implants (i.e., with regard to the latter, such as those having an implanted microphone and/or implanted battery). It is further noted that the teachings detailed herein are also applicable to other stimulating devices that utilize an electrical current beyond cochlear implants (e.g., auditory brain stimulators, pacemakers, etc.). Additionally, it is noted that the teachings detailed herein are also applicable to other types of hearing prostheses, such as, by way of example, direct acoustic cochlear stimulators, middle ear implants, etc. Indeed, it is noted that the teachings detailed herein are also applicable to so-called hybrid devices. In an exemplary embodiment, these hybrid devices apply both electrical stimulation and acoustic stimulation to the recipient. Any type of hearing prosthesis to which the teachings detailed herein and/or variations thereof that can have utility can be used in some embodiments of the teachings detailed herein.

In view of the above, it is to be understood that at least some embodiments detailed herein and/or variations thereof are directed towards a body-worn sensory supplement medical device (e.g., the hearing prosthesis of FIG. 1, which supplements the hearing sense, even in instances where all natural hearing capabilities have been lost). It is noted that at least some exemplary embodiments of some sensory supplement medical devices are directed towards devices such as conventional hearing aids, which supplement the hearing sense in instances where some natural hearing capabilities have been retained, and visual prostheses (both those that are applicable to recipients having some natural vision capabilities remaining and to recipients having no natural vision capabilities remaining). Accordingly, the teachings detailed herein are applicable to any type of sensory supplement medical device to which the teachings detailed herein are enabled for use therein in a utilitarian manner. In this regard, the phrase sensory supplement medical device refers to any device that functions to provide sensation to a recipient irrespective of whether the applicable natural sense is only partially impaired or completely impaired.

Still with reference to FIG. 1, the recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear channel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109, and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142, that is part of system 10 (along with cochlear implant 100), which, as described below, is configured to provide power to the cochlear implant (and, in some instances, data, which data a hearing percept evoked by the cochlear implant is based), where the implanted cochlear implant includes a battery that is recharged by the power provided from the external device 142.

In the illustrative arrangement of FIG. 1, external device 142 can comprise a power source (not shown) disposed in a Behind-The-Ear (BTE) unit 126. External device 142 also includes components of a transcutaneous energy transfer link, referred to as an external energy transfer assembly. The transcutaneous energy transfer link is used to transfer power and/or data to cochlear implant 100. Various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is typically a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present invention. In an exemplary embodiment, external device 142 also includes a transducer of a passive transcutaneous bone conduction device, as will be described in greater detail below.

Cochlear implant 100 comprises an internal energy transfer assembly 132 which can be positioned in a recess of the temporal bone adjacent auricle 110 of the recipient. As detailed below, internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire. In an exemplary embodiment, the turns extend about an implanted magnet. This magnet generates a permanent magnetic field that interacts with the permanent magnetic field generated by the magnet of the external device 142. This interaction both retains the external device 142 against the skin of the recipient, and thus in RF communication with the internal energy transfer assembly 132 via the transcutaneous RF link, and also aligns the external device 142 with the internal energy transfer assembly 132 (more specifically, aligns the turns of the external device with the internal device, due to the tendency of opposite poles of magnets to align with one another). That said, in an alternate embodiment, the external device 142 is held against the skin of the recipient via a non-magnetic retention system, such as, by way of example, so-called soft band retention (e.g., an elastic band extending about the head of the recipient which elastic band supports the external device 142 against the recipient) and/or so-called counseling arch retention (a solid structure that extends about at least a portion of the head that "clamps" against the head, which solid structure supports the external device 142). In an exemplary embodiment, a bone fixture (not shown) is utilized to fix the implanted magnet (and associated components, such as a vibratory plate used in conjunction with the bone conduction features of system 10, again described in greater detail below) to the mastoid bone.

Cochlear implant 100 further comprises a main implantable component 120 and an elongate electrode assembly 118. In some embodiments, internal energy transfer assembly 132 and main implantable component 120 are hermetically sealed within a biocompatible housing. In some embodiments, main implantable component 120 includes an implantable microphone assembly (not shown) and a sound processing unit (not shown) to convert the sound signals received by the implantable microphone in internal energy transfer assembly 132 to data signals. That said, in some alternative embodiments, the implantable microphone assembly can be located in a separate implantable component (e.g., that has its own housing assembly, etc.) that is in signal communication with the main implantable component 120 (e.g., via leads or the like between the separate implantable component and the main implantable component 120). In at least some embodiments, the teachings detailed herein and/or variations thereof can be utilized with any type of implantable microphone arrangement.

Main implantable component 120 further includes a stimulator unit (also not shown) which generates electrical stimulation signals based on the data signals. The electrical stimulation signals are delivered to the recipient via elongate electrode assembly 118.

Elongate electrode assembly 118 has a proximal end connected to main implantable component 120, and a distal end implanted in cochlea 140. Electrode assembly 118 extends from main implantable component 120 to cochlea 140 through mastoid bone 119. In some embodiments, electrode assembly 118 may be implanted at least in basal region 116, and sometimes further. For example, electrode assembly 118 may extend towards apical end of cochlea 140, referred to as cochlea apex 134. In certain circumstances, electrode assembly 118 may be inserted into cochlea 140 via a cochleostomy 122. In other circumstances, a cochleostomy may be formed through round window 121, oval window 112, the promontory 123, or through an apical turn 147 of cochlea 140.

Electrode assembly 118 comprises a longitudinally aligned and distally extending array 146 of electrodes 148, disposed along a length thereof. As noted, a stimulator unit generates stimulation signals which are applied by electrodes 148 to cochlea 140, thereby stimulating auditory nerve 114.

Some exemplary additional details of the external device 142 will now be provided.

As noted above, in an exemplary embodiment, system 10 has both the functionality of a cochlear implant and the functionality of a bone conduction device. In particular, the external device 142, in addition to an external component having the aforementioned functionality vis-à-vis supporting the functionality of the cochlear implant 100, is also a removable component of a passive transcutaneous bone conduction device. Before providing some specific details of the bone conduction functionality, some details of an exemplary system of evoking a hearing percept by bone conduction will now be described.

In an exemplary embodiment, external component 142 in general, and the headpiece supporting external coil 130 in particular (which headpiece is in signal communication with the BTE device 126 via wired or wireless communication, in at least some embodiments, while in other embodiments, the headpiece is a so-called button sound processor), is configured to generate vibrations and impart the vibrations into skin of the recipient at a location positioned behind outer ear 110.

As noted above, bone conduction functionality is such that the external device 142 is a passive transcutaneous bone conduction device utilizing, for example, electromagnetic actuators or piezoelectric actuators (or any other actuator that will enable the teachings detailed herein) or variations thereof where no active component (e.g., the electromagnetic or piezoelectric actuator) is implanted beneath the skin (it is instead located in the external device, such as the headpiece). In an exemplary embodiment, the implant 100 can include a magnetic pressure plate (a permanent magnet, ferromagnetic material, etc.), which magnetic pressure plate is or is not fixed to bone via a bone fixture or some other component. Some embodiments of the passive transcutaneous bone conduction systems are configured for use where the vibratory apparatus (e.g., an actuator located in the external device 142, along with the accompanying vibratory transmission components) is held in place by pressing the vibrator against the skin of the recipient. In an exemplary embodiment, the aforementioned magnetic coupling is used to hold a skin interface portion through which vibrations are transferred from the external device into the skin. Alternatively or in addition to this, a soft-band or other retention system is utilized.

Figure 2:
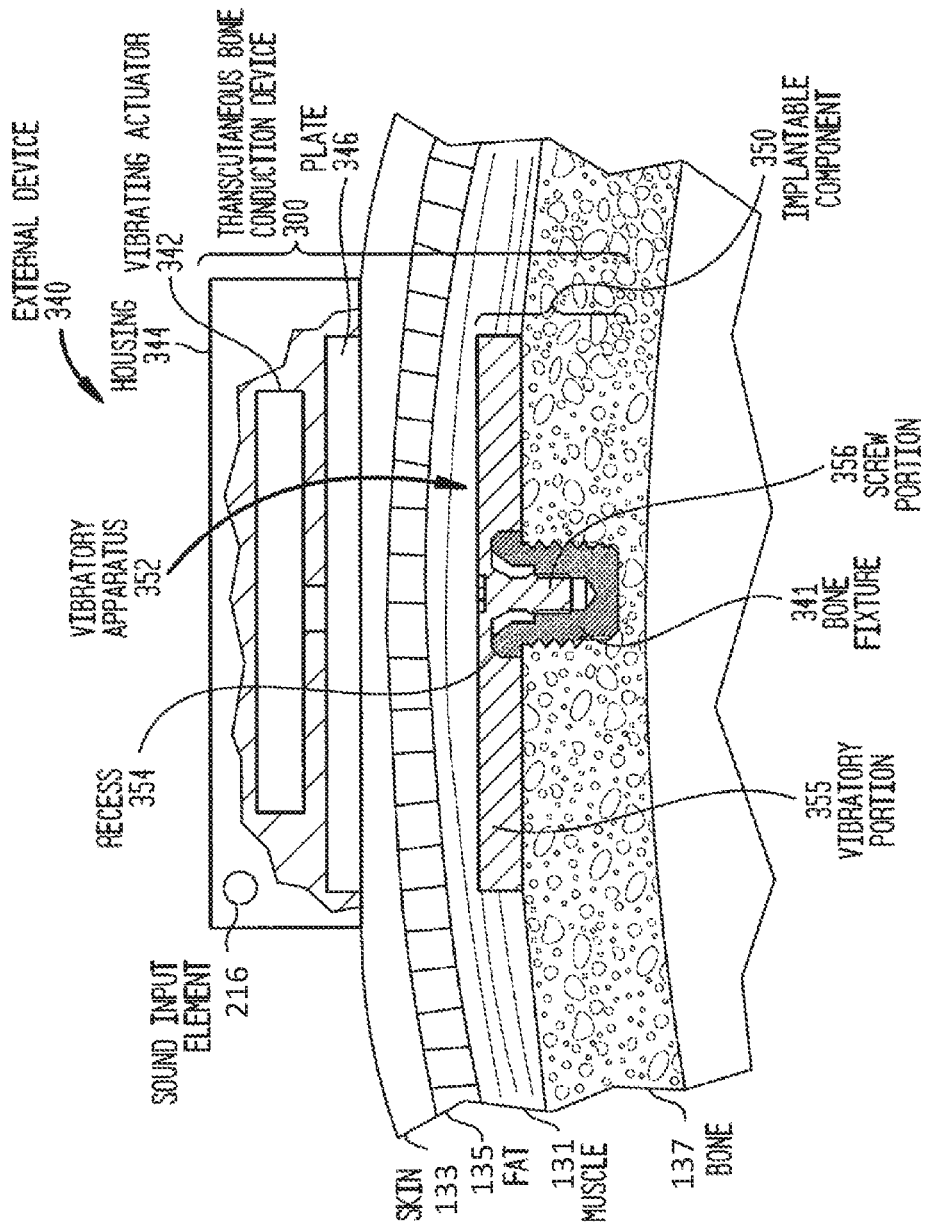
FIG. 2 is a functional view of an arrangement of an external component and an internal component in which the teachings detailed herein are applicable.

Some additional features of the bone conduction subsystem will now be described in terms of the functional schematic of FIG. 2. In this regard, FIG. 2 depicts an exemplary embodiment of a portion of an external device 340 of system 10, corresponding to external device 142. In an exemplary embodiment, external device 340 is configured such that it has all of the aforementioned functionality of the external component of the system 10 that includes the aforementioned cochlear implant and the aforementioned bone conduction device. With respect to the embodiment of FIG. 2, the external device 340 can be the complete device (i.e., there is no BTE utilized with the components shown in FIG. 2—an exemplary embodiment of such corresponds to a button sound processor system). That said, in an alternate embodiment, the external component 340 includes extra components, such as the BTE device 126. Any disclosure of an external device without a BTE device or another remote device remote from the headpiece (including a pocket worn or a belt worn or even a hand carried device, etc.) corresponds to a disclosure of a headpiece with such components, and visa-versa.

While the embodiments detailed herein are directed towards an external device 142 that utilizes a magnet to retain the device against the skin of the recipient, as noted above, in some alternate embodiments, the external device 142 does not have a magnet and/or is configured to be held against the skin of the recipient utilizing other retention systems, including non-magnetic retention systems. In this regard, the teachings detailed herein with regard to FIG. 2 are exemplary in nature and presented by way of example.

FIG. 2 depicts a functional schematic of an exemplary embodiment of a bone conduction system 300 usable in system 10 (system 300 is a sub-system of system 10, along with the cochlear implant sub-system) according to an embodiment. System 300 includes external device 340 (corresponding to, for example, at least a portion of element 142 of FIG. 1) and a portion of an implantable component 350 (corresponding to, for example, a portion of element 100 of FIG. 1—the integration of the implantable component 350 depicted in FIG. 2 and variations thereof with the cochlear implant 100 of FIG. 1 will be described below—in this regard, element 350 is more accurately defined as an implantable sub-component, but will be referred to herein as an implantable component for ease of discussion purposes), where the implantable component is located under skin 133, fat 135, and muscle 131 of the recipient, and fixed to bone 137 of the recipient (although in other embodiments, there is no fixation to the bone, at least not directly, as will be discussed below). The transcutaneous bone conduction device 300 of FIG. 2 is a passive transcutaneous bone conduction device in that a vibrating electromagnetic actuator 342 is located in the external device 340. Vibrating electromagnetic actuator 342 is located in housing 344 of the external component, and is coupled to plate 346. In an exemplary embodiment, the vibrating electromagnetic actuator 342 is a device that converts electrical signals into vibration. In operation, sound input element 216, such as a microphone (depicted as being carried by the headpiece of external component 340—in some alternate embodiments, the sound input element 226 is carried by the BTE device or other remote device), that converts sound into electrical signals. Specifically, the system 300 provides these electrical signals to vibrating actuator 342, or to a sound processor (not shown) that processes the electrical signals, and then provides those processed signals to vibrating electromagnetic actuator 342. The vibrating electromagnetic actuator 342 converts the electrical signals (processed or unprocessed) into vibrations. Because vibrating electromagnetic actuator 342 is mechanically coupled to plate 346 via a vibratory path extending from the actuator 342, the vibrations are transferred from the vibrating actuator 342 to plate 346 (and then into the skin 133, as the plate is in contact with the surface of the skin). Implanted plate assembly/vibratory apparatus 352 is part of the implantable component 350, and is made of a ferromagnetic material that may be in the form of a permanent magnet, that generates and/or is reactive to a magnetic field, or otherwise permits the establishment of a magnetic attraction between the external device 340 and the implantable component 350 sufficient to hold the external device 340 against the skin of the recipient, as will be detailed further below. Accordingly, vibrations produced by the vibrating electromagnetic actuator 342 of the external device 340 are transferred from plate 346 across the skin to plate 355 of implanted vibratory apparatus 352 (in an exemplary embodiment, the cochlear implant 100 includes a vibratory apparatus—more on this below). This can be accomplished as a result of mechanical conduction of the vibrations through the skin, resulting from the external device 340 being in direct contact with the skin and/or from the magnetic field between the two plates. These vibrations are transferred without penetrating the skin with a solid object such as an abutment as detailed herein with respect to a percutaneous bone conduction device. That said, in an alternate embodiment, there is no implanted vibratory apparatus implanted in the recipient.

As may be seen, the implanted plate assembly 352 is substantially rigidly attached to a bone fixture 341 in this embodiment. Plate screw 356 is used to secure plate assembly 352 to bone fixture 341. The portions of plate screw 356 that interface with the bone fixture 341 substantially correspond to an abutment screw as known in the art, thus permitting plate screw 356 to readily fit into an existing bone fixture used in a percutaneous bone conduction device or a transcutaneous bone conduction device. In an exemplary embodiment, plate screw 356 is configured so that the same tools and procedures that are used to install and/or remove an abutment screw (described below) from bone fixture 341 can be used to install and/or remove plate screw 356 from the bone fixture 341 (and thus the plate assembly 352).

Figure 3:
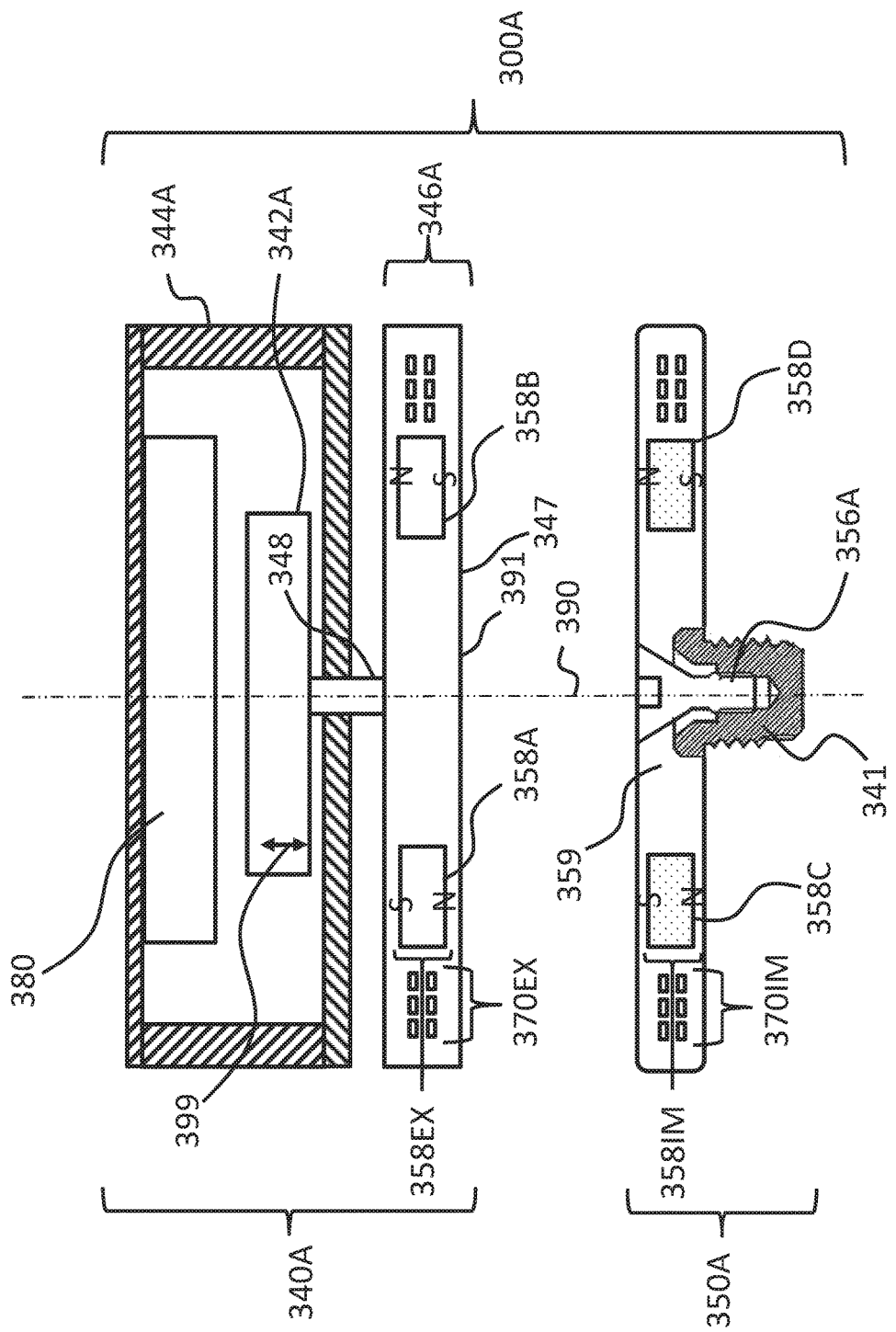
FIG. 3 is a structural view of an arrangement of an external component and an internal component in which the teachings detailed herein are applicable.

Referring now to FIG. 3, there is depicted a schematic of an exemplary system 300A having the functionality of system 300 of FIG. 2. The exemplary system 300A of FIG. 3 includes an external component 340A (or, in some embodiments, such as those where a BTE is used, a portion of an external component 340A) functionally corresponding to external component 340 of FIG. 2, and an implantable component 350A functionally corresponding to implantable component 350 of FIG. 2. (350A is more accurately defined as a sub-portion because there are additional components of the implantable component not shown in FIG. 3. Herein, 350A can be referred to as an implantable component 350A without reference to the sub-portion for ease of reference, but it is to be understood that there are additional components of the implantable component (e.g., the stimulator unit of implant 100). Additional details of some of these additional components will be described below).

In an exemplary embodiment, external component 340A has the functionality of a transducer/actuator, irrespective of whether it is used with implantable component 350A. That is, in some exemplary embodiments, external component 340A will vibrate whether or not the implantable component 350A is present (e.g., whether or not the static magnetic field extends to the implantable component 350A, as will be detailed below).

The external component 340A includes a vibrating actuator represented in black-box format by reference numeral 342A. In an exemplary embodiment, the vibrating actuator can be an electromagnetic actuator. Alternatively, in some alternate embodiments, the vibrating actuator 342A can be a piezoelectric actuator. Any type of an actuator that can enable the teachings detailed herein and/or variations thereof to be practiced can be utilized in at least some exemplary embodiments. That said, embodiments detailed herein will be described, by way of example, in terms of a vibrating electromagnetic actuator that utilizes a yoke about which is wound a coil that is energized and deenergized in an alternating manner so as to produce an electromagnetic field that interacts with permanent magnets that moves a seismic mass in a reciprocating vibratory matter in a direction of arrow 399.

Still with reference to FIG. 3, the vibrating electromagnetic actuator 342A is enclosed in a housing 344A, as can be seen. Housing 344A also contains, optionally, a sound processor 380, which is configured to receive a signal from a sound capture device (e.g., a microphone), and process that signal and output one or more signals so that a hearing percept can be evoked via bone conduction and/or via electrical stimulation according to the teachings detailed herein. In this regard, in this exemplary embodiment, the external device 340A corresponds to a so-called button sound processor. That said, in some alternate embodiments, the sound processor is not included within the housing 344A, but instead is located away from the housing (e.g., in the BTE device), and is in communication with the external device 340 via a wired connection and/or a wireless connection (more on this below). Still further, in some embodiments, two separate sound processors are utilized—one for evoking the electrical based hearing percept, and one for evoking the bone conduction hearing percept.

In some embodiments, the housing 344A is a hermetically sealed housing, while in other embodiments, it is not hermetically sealed. In at least some exemplary embodiments, the housing 344A is configured to provide the actuator 342A protection from shock and environmental conditions, etc. Any housing that can enable the teachings detailed herein and/or variations thereof can be utilized in at least some embodiments. In this regard, as can be seen, the transducer 342A is rigidly attached to skin interface portion 346A including a skin interface surface 391, which functionally corresponds to plate 346 of FIG. 2 detailed above, by structural component 348. In this exemplary embodiment, the structural component 348 provides a vibrational conduction path such that vibrations generated by actuator 342A are transferred from the transducer to the skin interface component 346A such that those vibrations can then be transferred into the skin of the recipient to ultimately evoke a hearing percept according to the teachings detailed herein and/or variations thereof. It is noted that in an exemplary embodiment, the housing 344A and/or the sound processor 380 and/or the sound capture device (e.g., microphone) are vibrationally isolated from the vibrational path from (and including) the actuator 342A, through the structure 348, to (and including) the skin interface component 346A. In an exemplary embodiment, external component 340A corresponds to a headpiece usable in conjunction with a BTE device or without a BTE device.

In at least some embodiments, skin interface portion 346A serves a dual role in that it both transfers vibrations from the external component 340A to the skin and also magnetically couples the external component 340A to the recipient. In this regard, as can be seen, skin interface portion 346A includes a housing 347 that includes an external magnet assembly 358EX. External magnetic assembly 358EX includes permanent magnets 358A and 358B having a North-South alignment as shown. While the embodiment depicted in FIG. 3 utilizes two magnets, as will be detailed below, in some other alternate embodiments, a single magnet is utilized. That said, in some other alternate embodiments, three or more external magnets are utilized. Any magnet configuration and/or arrangement that can enable the teachings detailed herein and/or variations thereof to be practiced can be utilized in at least some exemplary embodiments.

Also as can be seen, skin interface portion 346A also includes an inductance coil 370EX, which extends about the external magnet assembly 358EX. In an exemplary embodiment, inductance coil 370EX corresponds to the external coil 130 (hence the designation "EX"). This inductance coil 370EX is in signal communication with the sound processor 380 (whether the sound processor 380 is located within the housing 344A as depicted in FIG. 3, or located away from housing 344A, such as in the BTE device, etc.). Still further, in an exemplary embodiment, the inductance coil 370EX is also in signal communication (or at least can be placed into signal communication) with a power source so as to enable the inductance coil 370EX to provide a transcutaneous power link to the implantable component 100 so as to at least one of enable the recharging of an implanted battery or the like and/or to power a functional component thereof. That said, in some alternate embodiments, such as where the implantable device has the functionality of a totally implantable cochlear implant (e.g., there is an implanted microphone and an implanted sound processor), the inductance coil 370EX is not necessarily in signal communication with a sound processor. Instead, in at least some exemplary embodiments falling within the scenario, the inductance coil 370EX is in signal communication with the aforementioned power source to enable the aforementioned recharging/powering of the component of the implant 100.

As can be seen in FIG. 3, inductance coil 370EX extends completely about the external magnet assembly 358EX on planes that are normal to the longitudinal axis 390. In this regard, as can be seen, the inductance coil 370EX is a two-tiered inductance coil, having turns on a first tier and turns on a second tier below the first tier (relative to the frame of reference of FIG. 3). That said, in some exemplary embodiments, the inductance coil is a one tier coil. Any arrangement of an inductance coil that can enable the teachings detailed herein and/or variations thereof to be practiced can be utilized in at least some exemplary embodiments.

Skin interface portion 346A includes a skin interface surface 391 that is a bottom surface (relative to the frame of reference of FIG. 3) that is configured to interface with the exterior skin of the recipient. In this regard, skin interface portion 346A corresponds to plate 346 of FIG. 2 as described above. It is through skin interface portion 346A that vibrations generated by the electromagnetic actuator of the external component 340A are transferred from the external component 340A to the skin of the recipient to evoke a hearing percept. In an exemplary embodiment, the housing 347 of the skin interface portion 346A is made of a non-ferromagnetic material that is compatible with skin of the recipient (or at least is coated with a material that is compatible with skin of the recipient). In this regard, in at least some exemplary embodiments, the housing 347 is configured to substantially avoid influencing the magnetic flux generated by the permanent magnets of the external magnet assembly 358EX. Still further, in an exemplary embodiment, the housing 347 is configured to substantially avoid influencing the magnetic field generated by the inductance coil 370EX. Any arrangement of the housing 347 that will enable the teachings detailed herein and/or variations thereof can be practiced in at least some exemplary embodiments.

FIG. 3 also depicts an implantable component 350A corresponding to implantable component 350 of FIG. 2. In some embodiments, implantable component 350 includes an implantable magnet assembly 358IM that includes at least two permanent magnets 358C and 358D. Permanent magnet 358C has a North-South alignment in a first direction relative to a longitudinal axis of the electromagnetic actuator (the vertical direction of FIG. 3). In at least some exemplary embodiments, permanent magnets 358C and 358D are bar magnets connected to one another via the chassis 359 of the implantable component 350A. In an exemplary embodiment, the chassis 359 is a nonmagnetic material (e.g., titanium). It is noted that in alternative embodiments, other configurations of magnets can be utilized. Any configuration permanent magnet that can enable the teachings detailed herein and/or variations thereof to be practiced can be utilized in at least some embodiments.

That said, in an alternative embodiment, it is noted that the implantable component 350A does not include permanent magnets. In at least some embodiments, elements 358C and 358D are replaced with other types of ferromagnetic material (e.g., soft iron (albeit encapsulated in titanium, etc.)). Also, elements 358C and 358D can be replaced with a single, monolithic component (as is also the case with respect to elements 358A and 358B of the external magnet assembly 358EX. Any configuration of ferromagnetic material of the implantable component 350A that will enable the permanent magnets of the external component 340A to establish a magnetic coupling with the implantable component 350A that will enable the external component 340A to be adhered to the surface of the skin, as detailed herein, can be utilized in at least some embodiments.

Also, as can be seen, the implantable component 350A includes an inductance coil 370IM, which extends about the implantable magnet assembly 358IM. This inductance coil 370IM is configured to be energized or the like via the inductance coil of the external component 340A. In an exemplary embodiment, coil 370IM corresponds to the primary internal coil 136 (hence the designation "IM") of FIG. 1. The inductance coil 370IM is in signal communication with a functional component of the cochlear implant 100. In an exemplary embodiment, this can be an implanted battery of the cochlear implant 100. In an exemplary embodiment, this can be a stimulator of the cochlear implant 100 that receives the signal and then outputs electrical signal(s) to the electrode array to evoke an electrically induced hearing percept.

As can be seen in FIG. 3, inductance coil 370IM extends completely about the implantable magnet assembly 358IM on planes that are normal to the longitudinal axis 390 in this regard, as can be seen, the inductance coil 370EX is a two-tiered inductance coil, having turns on a first tier and turns on a second tier below the first tier (relative to the frame of reference of FIG. 3). That said, in some alternate embodiments, the coil is a one-tiered coil. Any arrangement of an inductance coil that can enable the teachings detailed herein and/or variations thereof to be practiced can be utilized in at least some exemplary embodiments.

As can be seen, implantable component 350A includes screw component 356A configured to screw into bone fixture 341 and thus secure the chassis 359 to the bone fixture 341, and thus to the recipient.

It is noted that in some alternate embodiments, the external component 340A can be utilized without the implantable component 350A (or, more accurately, the cochlear implant 100 does not include the implantable component 350A, or at least the non-RF coil components).

It is noted that while the embodiments depicted in FIG. 3 depicts the respective coils located outside of the respective outer diameters the respective magnet assemblies, in alternative embodiments, the coils can be located within the diameters of the magnet assemblies. Still further, in some exemplary embodiments, with respect to the longitudinal axis 390, the coils can overlap with the magnets. Any arrangements of the coils with respect to the magnets that can enable the teachings detailed herein can be utilized in at least some exemplary embodiments.

Figure 4:
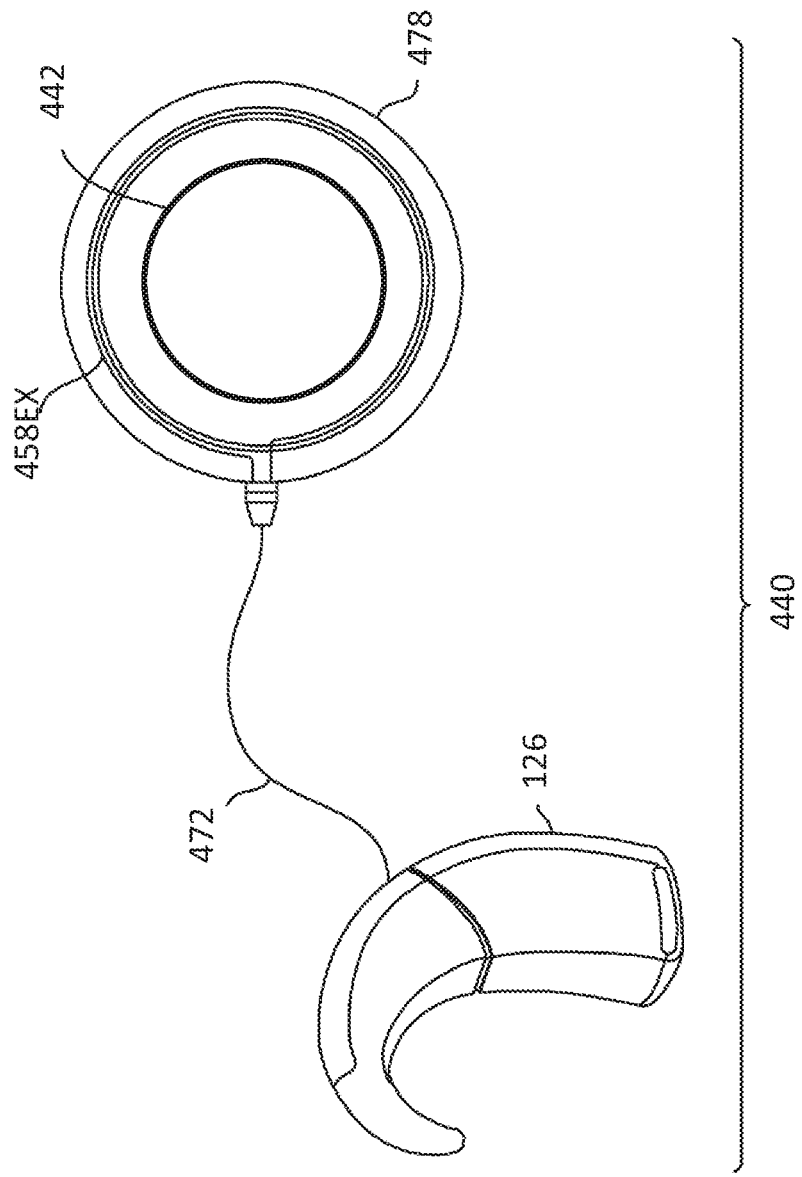
FIG. 4 is a perspective view of an exemplary external device according to an exemplary embodiment.

FIG. 4 depicts an exemplary external component 440 according to an exemplary embodiment utilizing a modified external component 340A. In this regard, external component 440 corresponds to external component 142 of the system 10. As can be seen, external component 440 includes a BTE device 126 which is connected via cable 472 to an exemplary headpiece 478 including an external inductance coil 458EX, corresponding to coil 370EX of FIG. 3. As illustrated, the external component 440 comprises the headpiece 478 that includes the coil 458EX and a magnet (or a plurality of magnets), which are not shown, but can correspond to the external magnets of FIG. 3, which magnet interacts with the implanted magnet (or implanted magnetic material) of the implantable component to hold the headpiece 478 against the skin of the recipient. In an exemplary embodiment, the external component 440 is configured to transmit magnetic data and/or power transcutaneously via coil 458EX to the implantable component, which includes an inductance coil. The coil 458X is electrically coupled to behind-the-ear (BTE) device 126 via cable 472. BTE device 126 may include, for example, at least some of the components of the external devices/components described below.

Headpiece 478 also includes transducer 442, corresponding to transducer 342A of FIG. 3. In this regard, in an exemplary embodiment, headpiece 478 corresponds to external component 340A of FIG. 3, without the sound processor 380. In embodiments without the sound processor 380, in some exemplary embodiments, a sound processor in the BTE 126 is utilized, while on other embodiments, an implanted sound processor is utilized. In embodiments where the headpiece 478 corresponds to external component 340A that includes the sound processor, headpiece 478 corresponds to external component 340A of FIG. 3.

Figure 5:
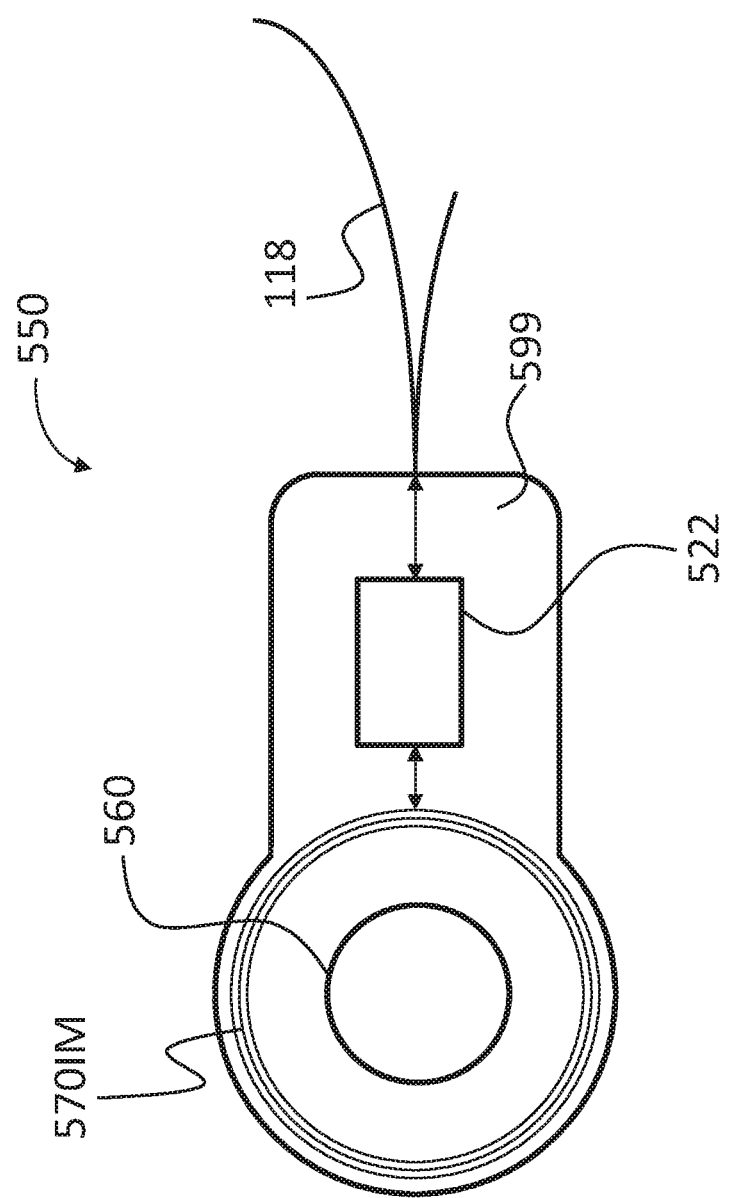
FIG. 5 is a top view of an exemplary implantable device according to an exemplary embodiment.

FIG. 5 depicts an exemplary high-level diagram of the implantable component 550 of the system 10, looking downward from outside the skull towards the skull. As can be seen, implantable component 540 (which corresponds to cochlear implant 100 of FIG. 1) includes a magnet 560 (or can be a plurality of magnets) that is surrounded by an implantable inductance coil 570IM (corresponding to coil 136 of FIG. 1) that is in two-way communication (although in other embodiments, the communication is one-way) with a stimulator unit 522, which in turn is in communication with the electrode assembly 118. The coil 570IM is presented in a conceptual manner. The magnet 560 interacts with the magnet(s) of the external component to retain the headpiece 578 (or any other external component) against the skin of the recipient so that transcutaneous inductance communication can take place between the two components via inductance communication between the external coil and the implanted coil.

In an exemplary embodiment of the embodiment of FIG. 5, the housing 599 of the implantable component 550 is made of an elastomeric material, such as silicone.

Figure 6:
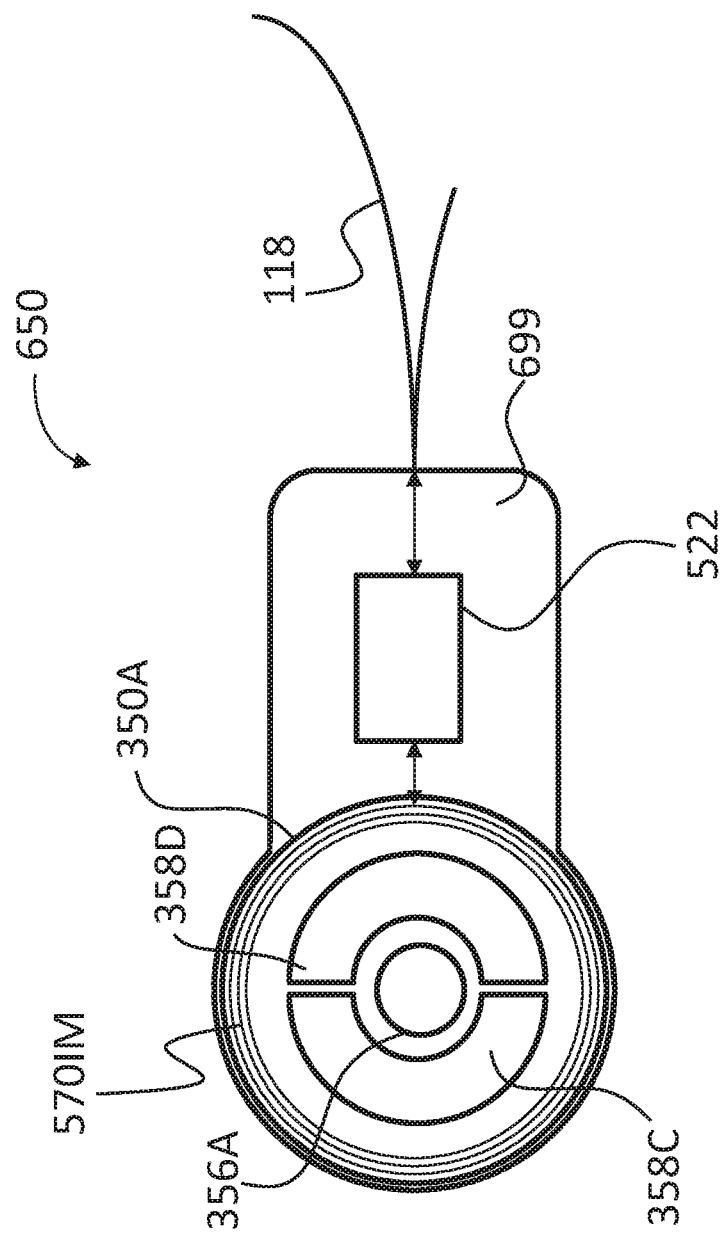
FIG. 6 is a top view of another exemplary implantable device according to an exemplary embodiment.

It is noted that magnet 560 is presented in a conceptual manner. In an exemplary embodiment, magnet 560 can correspond to a single disk magnet, or can correspond to the magnet assembly 370IM of FIG. 3. That said, in alternative embodiments, magnet 560 can correspond to other types of magnets assemblies or unitary magnets. With respect to the embodiment shown in FIG. 5, magnet 560 is presented without a chassis, as compared to the magnet assembly of FIG. 3, which is supported by chassis 359. In this exemplary embodiment, the magnet 560 corresponds to a traditional magnet arrangement in a cochlear implant where, for example, the magnet 560 is embedded in silicone of the housing 599. Still further, in an exemplary embodiment, the magnet 560 is not directly secured to bone of the recipient. That is, the magnet 560 is connected to the overall housing 599. In this regard, there is no screw 356A or bone fixture 341, as opposed to the embodiment depicted in FIG. 3. Conversely, in some other exemplary embodiments, a screw and a bone fixture are utilized to fix the magnet to the skull. Conversely, FIG. 6 depicts an implantable component 650 corresponding to implantable component 550, except that it utilizes the implantable component 350A (which includes the bone fixture and the screw). In an exemplary embodiment, a portion of the chassis (not labeled in FIG. 6, but corresponding to that of the implantable component of FIG. 3) is embedded in the housing 699, with openings in the housing to enable the screw 356A to pass through. In an exemplary embodiment, the chassis 359 can include a feature or the like to enable connection between the coil 570IM and the stimulator 522. Any arrangement that can enable the teachings detailed herein and/or variations thereof to be practiced can be utilized in at least some exemplary embodiments.

In an exemplary embodiment, chassis 359 can include or otherwise correspond to an implanted vibratory plate. That said, in some embodiments, the chassis 359 does not support the implanted coil. Instead, the chassis 359 can be a traditional implantable component of a percutaneous bone conduction device integrated into a traditional cochlear implant.

It is noted that all of the figures presented herein are conceptual FIGs. presented for purposes of discussion. Commercial embodiments corresponding to these FIGs. can be different from that depicted in the figures.

In view of the above, an exemplary embodiment includes a device, such as any of the external components or portions thereof detailed herein, that includes an inductive radio frequency (RF) communication coil (e.g., coil 370EX, coil 458EX, etc.), and a platform apparatus (e.g., housing 347, alone or along with a so-called soft pad that actually contacts the skin, etc., or at least the portion of the housing 347 that includes the skin interface surface (or the combination of such with a soft pad that actually contacts the skin), or a vibratory plate, etc.) which can be a part of a headpiece, such as headpiece 478, configured to at least one of be secured to or be coupled to an actuator (e.g., 342A) (either directly or indirectly) so as to establish a vibrational path from the actuator to a skin interface portion (e.g., surface 391) of the platform apparatus, wherein the coil is proximate the skin interface portion. In an exemplary embodiment, structure 348 is configured to snap-couple to housing 347, as will be described in greater detail below, and thus the platform apparatus is configured to be removably coupled to the actuator.

In this regard, an exemplary embodiment includes the utilization of a removable component of a percutaneous bone conduction device in a passive transcutaneous bone conduction system having a platform assembly which includes a coil. The removable component of the percutaneous bone conduction device 720 of FIG. 7 includes a coupling apparatus 740 configured to attach the bone conduction device 720 to an abutment connected to a bone fixture implanted in the recipient. The abutment extends from the bone fixture through muscle, fat, and skin so that coupling apparatus 740 may be attached thereto. Such a percutaneous abutment provides an attachment location for coupling apparatus 740 that facilitates efficient transmission of mechanical force from the bone conduction device 700. A screw holds the abutment to the bone fixture. As illustrated, the coupling apparatus 740 includes a coupling 741 in the form of a snap coupling configured to "snap couple" to a bone fixture system on the recipient.

In an embodiment, the coupling 741 corresponds to the coupling described in U.S. patent application Ser. No. 12/177,091 assigned to Cochlear Limited. In an alternate embodiment, a snap coupling such as that described in U.S. patent application Ser. No. 12/167,796 assigned to Cochlear Limited is used instead of coupling 741. In yet a further alternate embodiment, a magnetic coupling such as that described in U.S. patent application Ser. No. 12/167,851 assigned Cochlear Limited is used instead of or in addition to coupling 241 or the snap coupling of U.S. patent application Ser. No. 12/167,796.

The coupling apparatus 740 is mechanically coupled, via mechanical coupling shaft 743, to a vibrating actuator (not shown) within the removable component of the percutaneous bone conduction device 720. In an exemplary embodiment, coupling shaft 743 corresponds to structure 348 of FIG. 3, and the actuator, which is not shown, corresponds to actuator 342A. In an exemplary embodiment, the vibrating actuator is a device that converts electrical signals into vibration.

Figure 8:
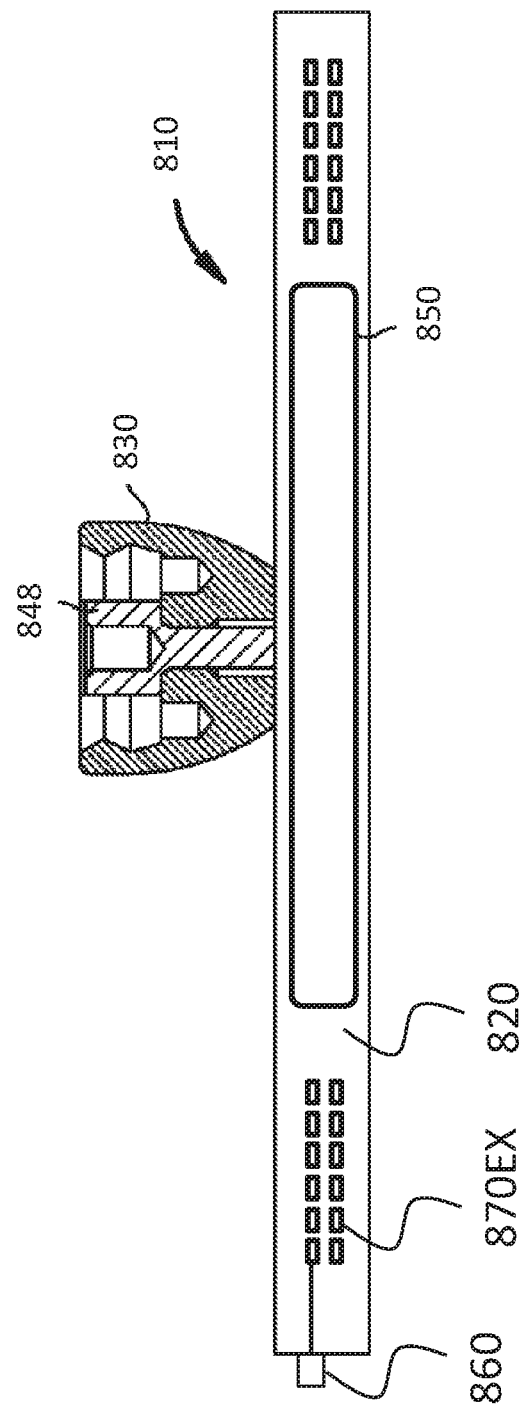
FIG. 8 is a side view of an exemplary platform usable with the component of FIG. 7 according to an exemplary embodiment.

Referring now to FIG. 8, there is a pressure plate assembly 810 as seen in FIG. 8 that, when coupled to the removable component of the percutaneous bone conduction device 720, results in an external device that corresponds to the external device 340A of FIG. 3. (In an exemplary embodiment, pressure plate assembly 810 corresponds to a platform assembly including a platform apparatus and an RF coil.)

Specifically, pressure plate 820 of pressure plate assembly 810 functionally corresponds to skin interface portion 346A detailed above with respect to FIG. 3, and the removable component of the percutaneous bone conduction device 720 functionally corresponds to the component(s) located above the skin interface portion 346A detailed above with respect to FIG. 3. An abutment 830 is attached to pressure plate 820 via abutment screw 848, as may be seen in FIG. 8. In an exemplary embodiment, abutment 830 is an abutment configured to connect to a bone fixture as known in the art. In some embodiments, abutment 830 is attached to pressure plate 820 by other means such as, for example, welding, etc., or is integral with the pressure plate 820. Any system that will permit vibrations from the removable component of the percutaneous bone conduction device 720 to be transmitted to the pressure plate 820 may be used with some embodiments. The abutment 830 permits the removable component of the percutaneous bone conduction device 720 to be rigidly attached to the pressure plate assembly 810 in a manner the same as or substantially the same as the removable component of the percutaneous bone conduction device 720 is attached to a bone fixture system. Still further, as can be seen, magnet 850 is included in the platform 810 so as to magnetically couple the platform 810 (and thus the removable component of the percutaneously bone conduction device 720) to the implantable component.

As can be seen, the pressure plate assembly 810 includes RF inductance coil 870EX, corresponding to coil 370EX of FIG. 3. In the exemplary embodiment depicted therein, there is a connector 860 configured to releasably connect to cable 472 which connects to a BTE device or the like. Connector 860 is in signal communication with the RF coil 870EX, as can be seen. That said, in an alternate embodiment, the connector 860 is a permanent connection to cable 472. In view of the above, an existing removable component of a percutaneous bone conduction device 720 can be utilized with a platform including an RF inductance coil according to the teachings detailed herein.

In an exemplary embodiment, the pressure plate assembly 810 in general, and the RF coil 870EX in particular, can be placed into signal communication via connector 860 to a sound processor located in the BTE device. Thus, the sound processor can output a signal that can be provided to the RF coil 870EX, which in turn generates an inductance field which is received by the implantable RF coil, which outputs a signal to the stimulator of the implantable component, which utilizes the received signal from the implantable RF coil to generate an electrical signal that is provided to the electrode array to evoke an electrically induced hearing percept. Moreover, in an exemplary embodiment, a second connector (not shown) can connect to a connector of the removable component of the bone conduction device (whether it be a removable component of a percutaneous bone conduction device or a removable component of a dedicated passive transcutaneous bone conduction device) such that signals from the sound processor of the BTE device can be sent to the pressure plate assembly, and then from the pressure plate assembly to the removable component of the bone conduction device. In this way, in an exemplary embodiment, a single sound processor of the BTE device can be utilized to generate signals upon which the electrical stimulation of the cochlear implant and the vibratory stimulation of the bone conduction device will be based. In an exemplary embodiment, the aforementioned second connector can be embodied in the abutment 830, where a corresponding connector can be located in the coupling apparatus 740 of the removable component of the bone conduction device.

A removable external component of the bone conduction device can have utilitarian value with respect to utilization of a headpiece in conjunction with a cochlear implant where bone conduction hearing percept's are not desired. That is, a headpiece corresponding to the pressure plate assembly 810 can be utilized to communicate with the cochlear implant without the removable component of the bone conduction device coupled thereto, and when it is desired to utilize the removable component of the bone conduction device to evoke a bone conduction hearing percept, the removable component of the bone conduction device can be attached to the pressure plate assembly 810.

Alternatively and/or in addition to this, the platform 810 in general, and the RF coil 870EX in particular, can be placed in signal communication with a sound processor located in the removable component of the bone conduction device. In this regard, connector 860 (or another, second connector) can be configured to connect to a cable that in turn connects to the removable component of the percutaneous bone conduction device 720. Thus, the sound processor of the removable component of the bone conduction device 720 can be utilized to provide a signal to the RF coil 870EX. That said, in an alternate embodiment, the connector 860 can be located on the abutment, and a corresponding connector located on the coupling apparatus 740 can couple with the connector 860 to establish the signal communication between the sound processor of the removable component of the percutaneous bone conduction device 720 and the RF coil of the platform 810. In alternative embodiments (or in addition to these embodiments), any of the aforementioned signal communications can be achieved via a wireless link.

While the aforementioned embodiments have just been described in terms of communication between sound processor(s) (and/or any intervening components) and the RF coil 870EX, alternatively or in addition to this, the communication is between a power source and the RF coil 870EX.

Such can have utilitarian value with respect to a totally implantable cochlear implant that does not rely on an external sound processor. (The management of the bone conduction sub-system and the cochlear implant sub-system can entail various options. While many embodiments that utilize simultaneous electrical stimulation of the cochlea and bone conduction stimulation of the cochlea will typically utilize the same sound processor upon which the electrical stimulation in the bone conduction simulation will be based, in some other embodiments, the bone conduction sub-system might be utilized independently of the cochlear implant sub-system, and thus separate sound processors might be utilized. (In some embodiments, the separate sound processors might be utilized simultaneously. Thus, embodiments can include two different sound processors, and, therefore, embodiments can be configured so that the various sound processors can be utilized, even if those sound processors will not be utilized simultaneously.)

Figure 9:
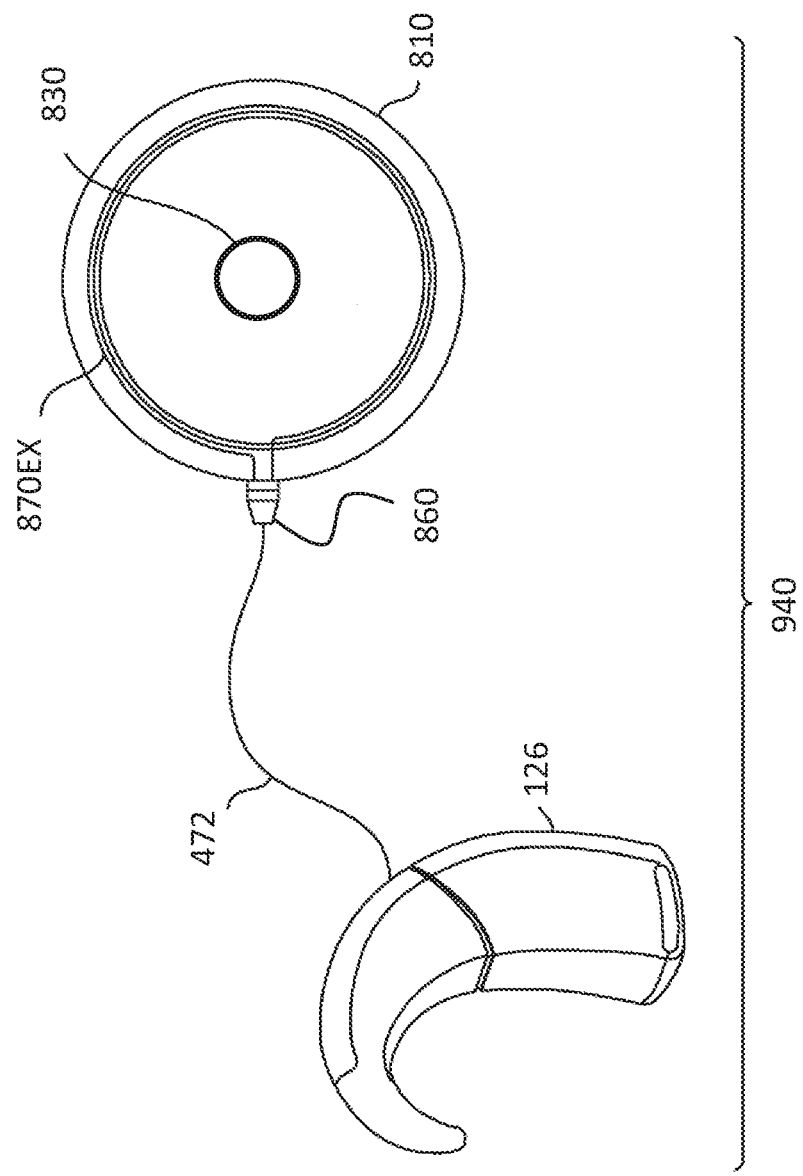
FIG. 9 is a perspective view of another exemplary external device according to an exemplary embodiment.

As noted above, in an exemplary embodiment, pressure plate assembly 810 can correspond to a headpiece of an external device corresponding to external device 142. In this regard, FIG. 9 depicts an exemplary external component 940 according to an exemplary embodiment utilizing a modified headpiece corresponding to pressure plate assembly 810 of FIG. 8 (without the removable component of the bone conduction device attached thereto). In this regard, external component 940 corresponds to external component 142 of the system 10. As can be seen, external component 940 includes the BTE device 126 which is connected via cable 472 to an exemplary headpiece 810 including the external inductance coil 870EX. Thus, in an exemplary embodiment, the removable component of the bone conduction device 720 can be variously removed and attached to the headpiece, depending on whether or not bone conduction hearing percept redeemed the utilitarian. It is noted that while the embodiment depicted in FIG. 8 includes an abutment component that extends from the pressure plate 820 in a somewhat extreme manner, in alternative embodiments, the pressure plate 820 is configured to receive the connecting assembly of the removable component of the bone conduction device 720 closer to the pressure plate 820. Indeed, in an exemplary embodiment, there is no abutment per se. Instead, the pressure plate 820 includes a cavity configured to receive the connection assembly in a snap coupling manner. Thus, in view of the above, in an exemplary embodiment, there is an actuator (e.g., the actuator of the removable component of the percutaneous bone conduction device 720) that is simply mechanically coupled to a platform apparatus (e.g., via the snap coupling), and the actuator is removably coupled to the platform apparatus (e.g., pressure plate assembly 810). Conversely, in an exemplary embodiment, there is an actuator that is complexly mechanically secured to the platform apparatus. In this regard, this is directed towards an exemplary scenario where the external device utilizes a true passive transcutaneous bone conduction device as opposed to utilizing a percutaneous bone conduction device configured to removably couple to the platform. Along these lines, the external component 340A of FIG. 3 can be considered to correspond to this embodiment, where structure 348 is configured to be non-removably connected to the skin interface portion 346A. By non-removably connected, it is meant that the connection is one that does not enable the recipient to readily disconnect the skin interface portion 346A from the structure 348 or otherwise remove the skin interface portion 346A from vibrational communication with the actuator. This does not exclude the ability for a technician or even the tinkerer to disassemble the skin interface portion 346A from the rest of the external component.

It is noted that in an exemplary embodiment, any of the teachings of U.S. Patent Application Publication No. 20120302823, entitled Convertibility of a Bone Conduction Device, filed on May 31, 2012, naming Dr. Marcus Andersson of Sweden, assigned to Cochlear LTD, can be combined with an inductance coil or RF coil according to the teachings detailed herein. Moreover, the teachings detailed in the aforementioned '823 publication can be used to implement features disclosed herein, such as the platform apparatus disclosed herein. Thus, in an exemplary embodiment, any teaching of a platform apparatus in the '823 publication can be used with any embodiment of the platform apparatus disclosed herein.

While the just detailed scenario describes the utilization of a dedicated passive transcutaneous bone conduction device, it is further noted that exemplary embodiments do include utilizing a removable component of a bone conduction device such that the feature of an actuator that is complexly mechanically secured to a platform is achieved. This can result, by way of example, by applying a form of glue or adhesive at the location where the removable component interfaces with the platform. Alternatively and/or in addition to this, a C spring or the like can be put into a hole that extends to the abutment and the coupling apparatus of the removable component so as to eliminate the snap coupling feature (or, more accurately, eliminate that functionality, at least while the C spring is present).

Figure 10:
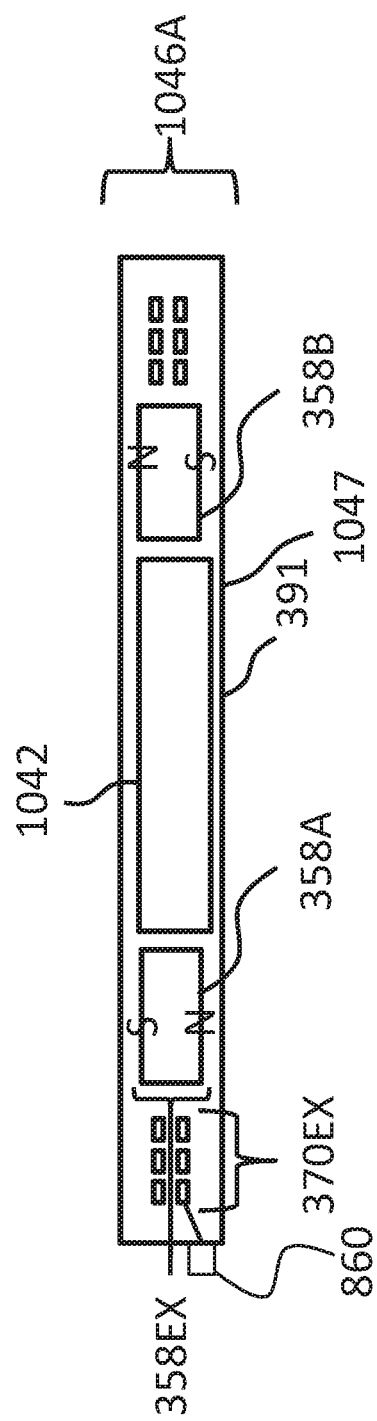
FIG. 10 is a side view of an exemplary headpiece according to an exemplary embodiment.

It is further noted that in an exemplary embodiment, the platform apparatus can be a platform assembly that includes the actuator and the RF coil. In this regard, FIG. 10 depicts a platform assembly in the form of a skin interface portion 1046A including a transducer 1042 corresponding to any of the transducers detailed herein and/or variations thereof, and a platform apparatus established by housing 1047, where the transducer 1042 is located in the housing 1047. In an exemplary embodiment, the skin interface portion 1046A corresponds to a headpiece connectable to a BTE device, or the like, via connector 860, which is configured to connect to a cable, such as cable 472. In this exemplary embodiment, the transducer 1042 is in signal communication with a sound processor of the BTE device, or at least in signal communication with another device that is in signal communication with the sound processor, and signals from the sound processor of the BTE device (or the device in communication with the sound processor) are utilized to control the transducer to vibrate to evoke a hearing percept based on the signals. Still further, in this exemplary embodiment, the coil 370EX is in signal communication with the sound processor of the BTE device, or at least in signal communication with another device that is in signal communication with the sound processor, and the signal from the sound processor of the BTE device (or another device in communication with the sound processor) is utilized to control the coil 370EX to generate an inductance field, which field is received by the implanted coils, which results in a signal generated by the implanted coils which is utilized as a basis to evoke an electrical hearing percept. It is noted that the aforementioned intermediate devices can be devices that are configured to change the signal from the sound processor to a signal that is compatible with the respective devices downrange from the signal processor. In this regard, in at least some embodiments, the output from the signal processor can be output that is readily usable by the transducer, but not readily usable by the external inductance coil or vice versa (or both). Thus, an intermediate device may transform the output into a signal that is usable by the respective devices.

Figure 11:
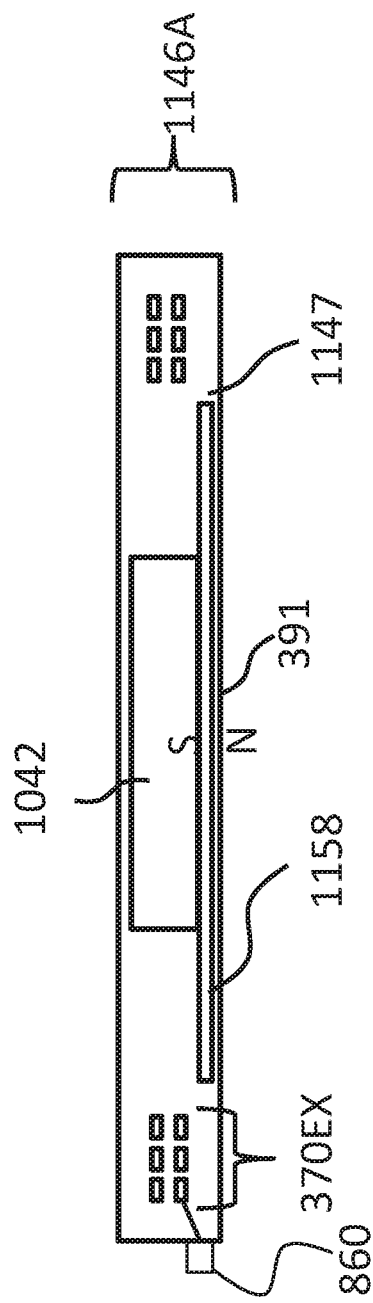
FIG. 11 is a side view of another exemplary headpiece according to an exemplary embodiment.

FIG. 11 depicts a platform apparatus in the form of a skin interface portion 1146A including the transducer 1042 corresponding to any of the transducers detailed herein and/or variations thereof located in a housing 1147. In this exemplary embodiment, instead of two separate magnets 358A and 358B, a single disk magnet 1158 is utilized, as seen. Transducer 1042 is located above the magnet 1158, as opposed to being surrounded by the magnets as is the case in the embodiment of FIG. 10.

Accordingly, in view of the above, in an exemplary embodiment, there is a device according to the teachings detailed herein that is configured to generate vibrations to evoke a bone conduction hearing percept at the same time that an inductive RF data signal is outputted from the coil.

It is further noted that in an exemplary embodiment, the external component 340A is a button sound processor. Accordingly, in an exemplary embodiment, there is a platform apparatus that is part of a button sound processor.

Figure 7:
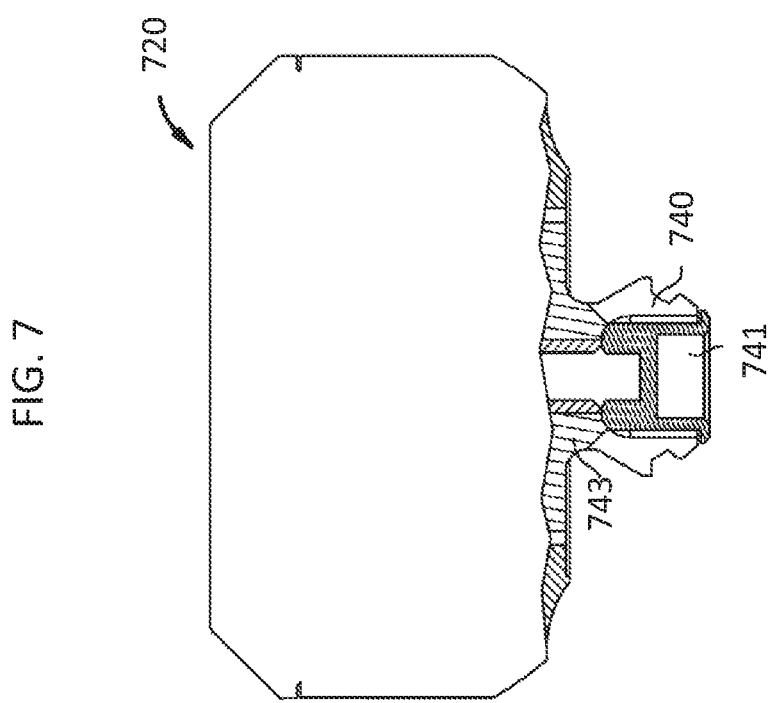
FIG. 7 is a side view of an exemplary removable component of a bone conduction device having utility in some exemplary embodiments.

In view of the above, embodiments include a device that utilizes a platform apparatus in vibrational communication with an actuator (where, as just noted, a platform assembly can include an actuator that is vibrational coupled to the platform apparatus), and also can include an actuator that is coupled to the platform, such as the embodiment of FIGS. 7 and 8, and can also include an actuator that is secured to the platform, such as is represented by the embodiment of FIG. 3), wherein the device is configured such that the platform apparatus is configured to vibrate to evoke a bone conduction hearing percept via transfer of the vibrations from the platform apparatus to skin of the recipient.

It is noted that in at least some exemplary embodiments, it is possible that the vibrations generated by the actuator and conducted to the platform apparatus can deleteriously affect the inductance communication as a result of vibrations of the external coil. Accordingly, in an exemplary embodiment, the external coil is separate from the platform apparatus. By way of example, a separate assembly supporting an external inductance coil can extend about the platform (which can include the magnets and/or the magnets can be a part of the separate assembly). That said, in an alternate embodiment, the external inductance coil is still part of the platform apparatus, but the coils are vibrationally isolated from the vibrations that are imparted into the platform apparatus by the actuator. Any arrangement that can enable the external coils to be vibrationally isolated, or at least partially vibrationally isolated, from the vibrations generated by the actuator can be utilized in at least some exemplary embodiments.

It is also noted that with respect to the implantable component, the implanted coils can be vibrationally isolated from the vibratory components (e.g., the implanted magnet and/or any implanted plates, etc.) of the implant utilized to execute bone conduction.

In view of the above, an exemplary embodiment includes a transcutaneous radio frequency (RF) communication system, such as that of system 10 of FIG. 1 above, comprising an external component (e.g., external device 340A) including a first RF communication apparatus (e.g., coils 370EX), a transducer configured to at least one of convert electrical input into mechanical output (e.g., actuator 342A) or mechanical input into electrical output (which can be a device having the same configuration as actuator 342A, but used in a reverse mode, where vibrations are imparted into the transducer and an electrical signal is outputted, or can be another transducer configured especially for such). In this exemplary embodiment, the external component further includes a first magnetic apparatus, such as by way of example, the combination of 358A and 358B, or a single magnet thereof (or another magnet, such as magnet 850). That said, the first magnetic apparatus need not be a magnet, but could be any material that an implanted magnet will attract (e.g., a ferromagnetic material). Hereinafter, the first magnetic apparatus will be referred to as a first magnet apparatus, but it is noted that alternate embodiments need not use a magnet.

Still further, with respect to the exemplary transcutaneous radiofrequency communication system described in the paragraph immediately above, the exemplary system further includes an implantable component (e.g., implantable component 350A of FIG. 3, etc.), including a second RF communication apparatus (e.g., coil 370IM), and a second magnetic apparatus (e.g., 358C or 358D, or a single one of those, or magnet 560, etc.). That said, the second magnetic apparatus need not be a magnet, but could be any material that an external magnet will attract (e.g., a ferromagnetic material). Hereinafter, the second magnetic apparatus will be referred to as a second magnet apparatus, but it is noted that alternate embodiments need not use a magnet if the external device includes a magnet.

In this exemplary embodiment, the system is configured to hold the external component to skin of the recipient via magnetic attraction between the first magnet apparatus and the second magnet apparatus with a force of between and including about 0.75N and about 1.05N when the first magnet is separated from the second magnet by about 1 mm to about 10 mm of human skin.

As will be described in greater detail below, in some exemplary embodiments, because the bone conduction system used is configured to only evoke hearing percepts at certain frequencies (e.g., at or below about 2000 Hz), the seismic mass of the transducer can be lower than that which would be the case in the scenario where the transducer was used (or is configured to be used) to evoke hearing percepts at all frequencies (within the audible spectrum), or at least at frequencies above the various lower frequencies. Thus, in some exemplary embodiments, the actuator that is utilized to evoke the bone conduction hearing percepts is lighter than that which would otherwise be the case, all things being equal, for a system that evoked the hearing percepts at all frequencies, or at least at frequencies above the various lower frequencies. Accordingly, the magnetic retention force utilized by the external component (e.g., the headpiece) can be lower than that which would otherwise be the case, all other things being equal. Thus, the aforementioned magnetic force ranges have utilitarian value relative to that which would be the case for actuators that evoke hearing percepts at the other frequencies.

In an exemplary embodiment of this system, the aforementioned first magnet apparatus (the magnet of the external component) is a Neodymium magnet. In an exemplary embodiment, the magnet has a magnetic field strength of about 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950 or about 2000 mT or any value or range of values therebetween in 1 mT increments (e.g., 1111 mT, about 1591 mT, about 1066 mT to about 1492 mT, etc.). In an exemplary embodiment, the first magnet is a circular plate magnet having a diameter of about 10 mm to about 30 mm or any value or range of values therebetween in about 0.01 mm increments and a thickness of about 1 mm to about 10 mm or any value or range of values therebetween in about 0.01 mm increments.

In an exemplary embodiment of this RF communication system, an input/output path of the transducer is at least approximately concentric with the first magnet apparatus, and the first RF communication apparatus includes a first RF coil that extends about the first magnet apparatus and is at least approximately concentric with the first magnet apparatus. This is seen in any of the above embodiments depicted herein. With respect to the embodiment of FIG. 3, where the output of the actuator 342A extends along structure 348, the magnets 358A and 358B and the coil 370EX are concentric thereabout. This is also the case with the embodiment of FIGS. 7 and 8, where the output from the transducer travels through coupling apparatus 740, which is concentric with magnet 850 when the coupling apparatus 740 is attached to abutment 830.

In at least some exemplary embodiments of the aforementioned RF transmission system, the transducer is an actuator of a bone conduction device according the teachings detailed herein. That said, as noted above, in an alternate embodiment, the transducer is configured to receive vibrations transmitted through the skin to the surface 391 or whatever skin interface portion there exists in the external device, which vibrations are received by the external device and transmitted by the external device to the transducer. The transducer is configured to convert the mechanical energy into electrical output signals, which are outputted to a device such as a process, or the like, which can read the signals and evaluate the signals.

Still with respect to at least some exemplary embodiments of the aforementioned RF transmission system, the external device is configured to vibrate, thereby evoking a hearing percept as detailed herein. Consistent with the teachings above, in at least some exemplary embodiments of the aforementioned RF transmission system, the implantable component further comprises a receiver/stimulator of a cochlear implant, of which the second RF communication apparatus is apart. An exemplary embodiment of such is depicted in FIGS. 5 and 6. In this exemplary embodiment, the receiver/stimulator is configured to use signals received by the second RF communication apparatus generated by the first RF communication apparatus, and, based upon the signals received by the second RF communication apparatus, generate an electrical current to evoke an electrical based hearing percept.

It is noted that the aforementioned first RF communication apparatus includes a first RF coil (e.g., coil 370EX) that is concentric with the first magnet apparatus (e.g., magnet assembly 358EX). It is further noted that the second RF communication apparatus includes a second RF coil (e.g., coil 370IM) that is concentric with the second magnet apparatus (e.g., magnet assembly 358IM). The RF transmission system is configured such that an input/output path of the transducer is at least approximately concentric with the first magnet apparatus and the second magnet apparatus, and the first RF coil is at least approximately concentric with the second RF coil when the external component is adhered to the recipient via the magnetic attraction. As detailed above, in an exemplary embodiment, this can be achieved via the utilization of one or more magnets and the implanted component and one or more magnets in the external component, where the magnetic poles of the magnets are aligned so as to force the external component to align with the implanted component.

Figure 12:
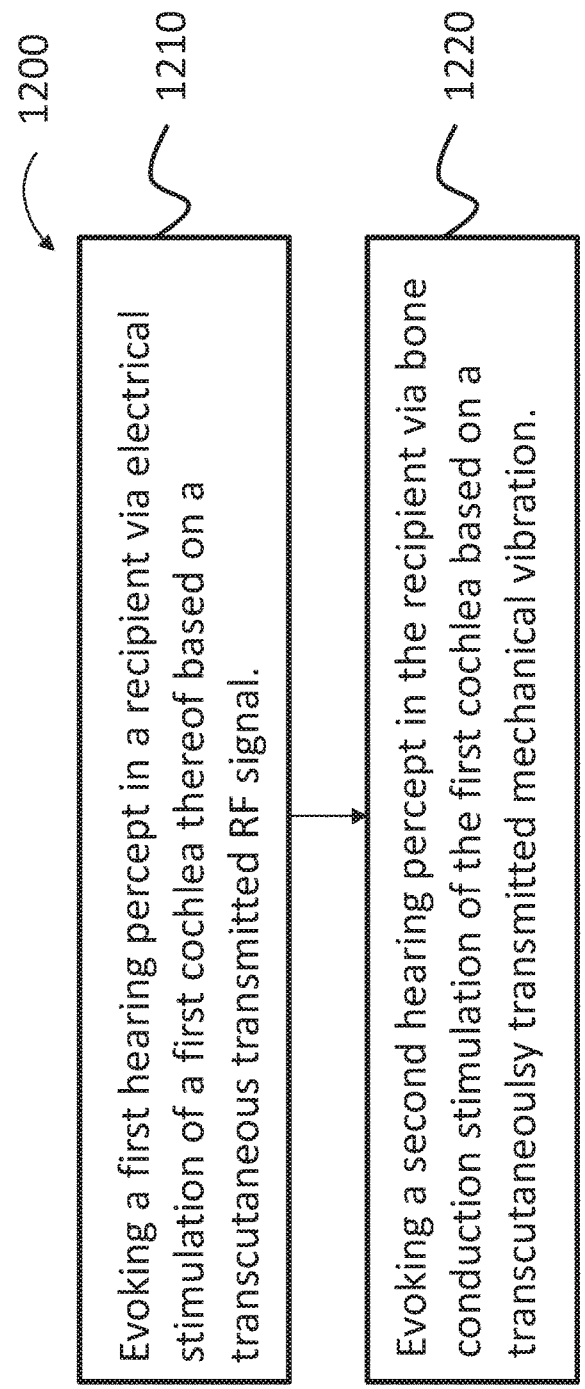
FIG. 12 presents a flowchart for an exemplary algorithm according to an exemplary method.

Referring now to FIG. 12, which presents an exemplary algorithm 1200 according to an exemplary method, according to an exemplary embodiment, there is a method 1200 which entails method action 1210, which entails evoking a first hearing percept in a recipient via electrical stimulation of a first cochlea thereof based on a transcutaneous transmitted RF signal. In an exemplary embodiment, method action 1210 is executed utilizing a cochlear implant, such as cochlear implant 100. Method 1100 further includes method action 1220, which entails evoking a second hearing percept in the recipient via bone conduction stimulation of the first cochlea based on a transcutaneously transmitted mechanical vibration. In this exemplary method, the transcutaneously transmitted mechanical vibration transmitted in method action 1220 and the transcutaneously transmitted RF signal transmitted in method action 1210 enter the skin of the recipient at least at locations that are proximate one another. It is noted that method actions 1210 and 1220 can be executed such that method action 1220 is executed before method action 1210, and method action 1210 can be executed at the same time as method action 1220.

Accordingly, in view of the above, an exemplary embodiment entails evoking two types of hearing percepts (electrical based and vibratory based) in the same cochlea, and thus exemplary embodiments can have utilitarian value with respect to harnessing residual hearing capability of a given cochlea, and, in some instances, preserving residual hearing in the cochlea (as opposed to "abandoning" the cochlea to purely electrical stimulation).

It is noted that in at least some exemplary embodiments, method 1200 is executed utilizing any of the devices, systems, and/or methods detailed herein, such as, by way of example, the external device 340A of FIG. 3 detailed above and/or any of the various permutations thereof disclosed herein, or any other variations thereof that can enable the method 1200 to be executed.

In an exemplary embodiment of method 1200, the transcutaneously transmitted mechanical vibration and the transcutaneously transmitted RF signal enter the skin of the recipient at the same location. In an exemplary embodiment of method 1200, the transcutaneously transmitted RF signal is generated by an inductance field, and the transcutaneously transmitted mechanical vibrations enter the skin of the recipient at a location that is at least approximately concentric with the generated inductance field.

In an exemplary embodiment of method 1200, the recipient includes a second cochlea in addition to the first cochlea, and the transcutaneously transmitted mechanical vibration and the transcutaneously transmitted RF signal enter the skin of the recipient at locations closer to the first cochlea than to the second cochlea. In this regard, by way of example, this aforementioned feature of method 1200 can be executed utilizing the external device 340A of FIG. 3.

In an exemplary embodiment of method 1200, the recipient that has the second cochlea is subjected to the transcutaneously transmitted mechanical vibration and the transcutaneously transmitted RF signal of method actions 1220 and 1210, such that those vibrations and signals enter the skin of the recipient at locations closer to the second cochlea than to the first cochlea.

It is noted that in an exemplary embodiment, there can be utilitarian value with respect to utilizing the aforementioned system 10 as detailed herein and/or variations thereof to implement a so-called bimodal hearing prosthesis. In the exemplary embodiments detailed herein, system 10 can be a bimodal hearing prosthesis that enables a bone conduction hearing percept (due to the vibrator/actuator) and an electrical based hearing percept (due to the cochlear implant). In an exemplary embodiment, a single unified sound capture system can be utilized upon which to base the bone conduction hearing percept and the electrical based hearing percept. That is, in an exemplary embodiment, the same microphone (or microphone array in the case of beamforming or the like) can be utilized to capture sound, and the signal can be sent to one or more sound processors, which process the signal from the microphone and in turn, output signal(s) that are utilized by the respective bone conduction sub-system and the cochlear implant sub-system to evoke respective hearing percepts. In an exemplary embodiment, a single/common sound processor is utilized for both sub-systems. That said, in an alternative embodiment, separate and distinct sound processor systems are utilized (note that the separate systems can be based in a single chip, or the like). Still further, in an exemplary embodiment, if the same sound processor is utilized, the output thereof can be sent to different units/processors (e.g., firmware chips, etc.) that convert the output of the sound processor into a signal that is usable by the respective sub-systems (e.g., to power and/or control the actuator of the bone conduction sub-system, and to control the stimulator of the implantable component of the cochlear implant).

In an exemplary embodiment, the teachings detailed herein and/or variations thereof can have utilitarian value with respect to providing artificial based hearing percepts in recipients that have so-called residual hearing. By way of example, some recipients are human organisms that have one or more cochleae that have limited but some functionality. In an exemplary embodiment, a given cochlea might no longer be functional with respect to high-frequency sounds and/or mid-frequency sounds, but might still be functional with respect to low-frequency and/or mid-frequency sounds. In an exemplary embodiment, the electrode array is a so-called short electrode array or the like. That is, in an exemplary embodiment, the electrode array extends only a limited amount into the damaged cochlea such that the electrode array is located only at those portions of the cochlea that correspond to the frequencies of the hearing loss (e.g., the high frequencies and/or the high and medium frequencies). This as contrasted to an electrode array that is "fully" inserted into the cochlea so as to enable the location of a hearing percept at the lower frequencies (or lower and middle frequencies). However, in some alternate embodiments the electrode array is a full length array implanted in a cochlea in a manner that preserves residual hearing at locations proximate the full length array.

Because in at least some exemplary scenarios of the utilization of the embodiments detailed herein and/or variations thereof, the cochlea cannot react to the medium and/or high frequencies, bone conduction techniques will not result in the evocation of a hearing percept that these frequencies. Thus, the cochlear implant is utilized to evoke a hearing percept at these frequencies. Conversely, because the electrode array of the cochlear implant, at least in some embodiments, is not located at the portions of the cochlea that have the residual hearing (e.g., the portions of the cochlea associated with the low or low and middle frequencies), the cochlear implant sub-system will not be able to provide electrical stimulation to evoke a hearing percept at these frequencies. Alternatively, even if such can be done (electrical based hearing percepts at the lower or lower and mid frequencies) despite the limited location of the electrode array, due to the flow of current from electrodes of the electrode array over greater distances, or in the alternative, in embodiments where the electrode array is fully implanted, but residual hearing is preserved due to the efforts to advance the art by entities such as the assignee of the present application, there can still be utilitarian value with respect to providing a bone conduction hearing percept that these frequencies in lieu of and/or in addition to providing an electrically based hearing percept at these frequencies.

Accordingly, in view of the above, in an exemplary embodiment, by way of example, the bone conduction hearing percepts that are evoked are limited to frequencies at the low and/or medium and low frequencies.

Figure 13:
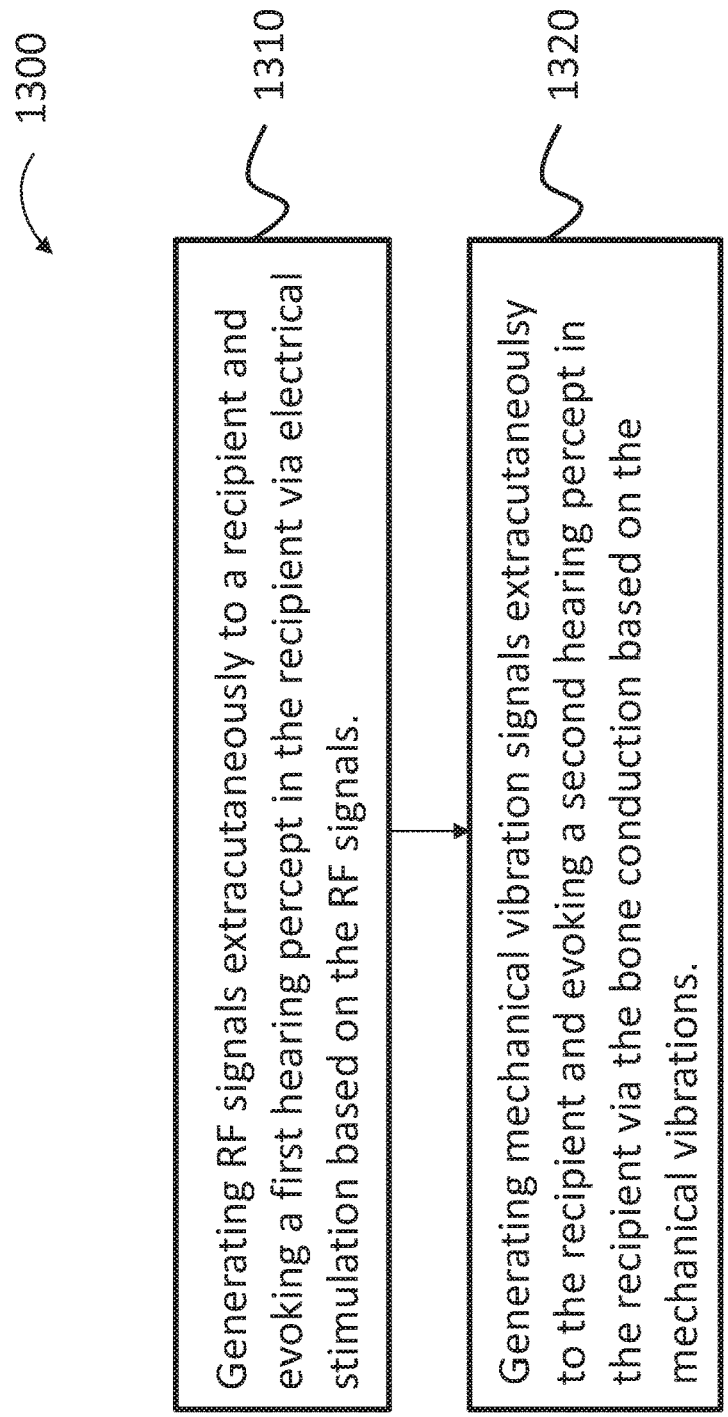
FIG. 13 presents a flowchart for an exemplary algorithm according to an exemplary method.

In view of this, now with reference to FIG. 13, which presents an exemplary algorithm 1300 according to an exemplary method, there is a method 1300 which entails method action 1310, which entails generating RF signals extracutaneously to a recipient (e.g., using coil 370EX) and evoking a first hearing percept in the recipient via electrical stimulation based on the RF signals (e.g., using the implanted cochlear implant 100 of FIG. 1, etc.). Method 1300 further includes method action 1320, which entails generating mechanical vibration signals extracutaneously to the recipient (e.g., using the transducer 342A, etc.) and evoking a second hearing percept in the recipient via the bone conduction based on the mechanical vibrations. In exemplary embodiments of method 1300, the method is executed by limiting the generated vibrations to about 2000 Hz and below. It is noted that method actions 1310 and 1320 can be executed such that method action 1320 is executed before method action 1310, and method action 1310 can be executed at the same time as method action 1320.

In an exemplary embodiment, the mechanical vibrations are generated using a bone conduction system which is limited to generating vibrations of about 2000 Hz and below by at least one of structure, circuitry or programming. In an exemplary embodiment, the system is limited to generating vibrations below about 200 Hz, 300 Hz, 400 Hz, 500 Hz, 600 Hz, 700 Hz, 800 Hz, 900 Hz, 1000 Hz, 1100 Hz, 1200 Hz, 1300 Hz, 1400 Hz, 1500 Hz, 1600 Hz, 1700 Hz, 1800 Hz, 1900 Hz, or below about 2000 Hz or any value or range of values therebetween in 1 Hz increments (e.g., below about 1555 Hz, below about 1776 Hz, etc.) In this regard, by way of example, with respect to mechanical limitations, the actuator can be dampened. Still with respect to the mechanical limitations, by way of example, the component that supports the component of the actuator (e.g., the seismic mass) that moves relative to the other components (e.g., the skin interface portion), such as the spring, is of a configuration where the system is such that any energy that the system could provide to the actuator is not enough to cause the actuator to vibrate at a rate higher than about 2000 Hz. With respect to circuitry, in an exemplary embodiment, the system is configured such that the system will not send an output signal to the actuator that will cause the actuator to vibrate more than about 2000 Hz, even though the actuator is physically configured to vibrate higher than that if a different signal was applied thereto. With respect to programming, in an exemplary embodiment, the system is programmed with the governor so as to massage or otherwise process the data so that no output will be provided to the actuator that will cause the actuator to vibrate at a rate higher than about 2000 Hz, even though the overall circuitry is configured to provide such an output if the programming of the system would permit such.

In some exemplary embodiments, because the bone conduction system is configured to only evoke hearing percepts at the aforementioned frequencies and below (or at least only used to do so), the seismic mass of the transducer can be lower than that which would be the case in the scenario where the transducer was used (or is configured to be used) to evoke hearing percepts at frequencies above (including well above) the aforementioned limited ranges.

In at least some exemplary embodiments, because the bone conduction system (sub-system) is configured such that a hearing percept will not be evoked utilizing transducer vibrations greater than 2000 Hz (or greater than one or more of the aforementioned limits), the actuator that is utilized to evoke the bone conduction hearing percepts can be lighter than that which would otherwise be the case, all things being equal. Accordingly, the magnetic retention force utilized by the external component (e.g., the headpiece) is lower than that which would otherwise be the case, all other things being equal.

Accordingly, in at least some exemplary embodiments, there is a headpiece including the actuator and the RF coils as detailed herein, which can be a button sound processor or can be a headpiece in communication with a sound processor in the BTE, which also includes a magnet apparatus configured to adhere the headpiece to the skin of the recipient. In an exemplary embodiment, the magnet apparatus is such that the magnet apparatus would not adhere the BTE to the recipient in a scenario where the actuator thereof was not limited to generating vibrations of about 2000 Hz and below, and the resulting hearing percept for a 50 percentile male or female of U.S. citizenry or a 50 percentile male or female of European Union citizenry (as of the filing date of this application) of 18 years of age who is a native language speaker of a given language at one or more of the aforementioned frequencies would be effective for the 50 percentile recipient to understand the given language based solely on bone conduction, all other things being equal (e.g., a standardized language comprehension test would be passed at least more than 50% of the time).

In an exemplary embodiment, the magnet apparatus is such that the magnet apparatus would not adhere the BTE to the recipient in a scenario where the actuator thereof was configured to provide vibrations at least in a range from about 2000 Hz to at least 5000 Hz, or to 6000 Hz, or to 7000 Hz, or to 8000 Hz, or to 9000 Hz, or to 10000 Hz, or more, with respect to a 50 percentile male or female of U.S. citizenry or a 50 percentile male or female of European Union citizenry (as of the filing date of this application) of 18 years of age, all other things being equal.

It is also noted that the aforementioned scenarios are also applicable to the magnet system of the combined implant and the external component, in at least some embodiments. Still further, in an exemplary embodiment, the magnet apparatus of the aforementioned headpiece could still be such that the magnet apparatus would still adhere the headpiece to a recipient in a scenario where the actuator thereof was not limited to generating vibrations of about 2000 Hz and below (e.g., even if the actuators were identical, mechanically, structurally, weight wise, etc.), but the resulting hearing percept for a 50 percentile male or female of U.S. citizenry or a 50 percentile male or female of European Union citizenry (as of the filing date of this application) of 18 years of age who is a native language speaker of a given language at one or more frequencies of about 2500 Hz, 3000 Hz, 3500 Hz, 4000 Hz, 4500 Hz, 5000 Hz, 5500 Hz, 6000 Hz, 6500 Hz, or 7000 Hz, or more, or any value or range of values therebetween in 1 Hz increments would be ineffective for the 50 percentile recipient to understand the given language based solely on bone conduction, all other things being equal (e.g., a standardized language comprehension test would not be passed at least more than 50% of the time). (In an alternate exemplary embodiment, the magnet apparatus is the weaker magnet apparatus detailed above.) This is because in an exemplary embodiment, the higher frequencies are attenuated by the tissue overlying the implanted component, and the magnetic attraction between the implant and the external component is weaker than that which would otherwise bet eh case. It is also noted that the aforementioned scenarios are also applicable to the magnet system of the combined implant and the external component, in at least some embodiments.

In an exemplary embodiment, the RF inductance coil used to generate the RF signals in method action 1310 and the actuator used to generate the vibrations in method action 1320 are adhered to the recipient via the same magnet system (e.g., magnet apparatus 358EX in conjunction with magnet apparatus 358IM or an implanted ferromagnetic material, etc.).

Moreover, in an exemplary embodiment, the RF inductance coil used to generate the RF signal and the actuator used to generate the vibrations respectively in method actions 1310 and 1320 are integrated into a button sound processor (e.g., 1046A or 1146A, with or without a wired connection with the BTE device or some other remote device or with or without a wireless connection with the BTE device or some other remote device, etc.).

It is noted that the aforementioned frequency limitations and disclosure related to the frequencies described above are also applicable to method 1200, in at least some exemplary embodiments.

That said, in an alternate exemplary embodiment, there is a method that entails vibrating the actuator at frequencies higher than about 2000 Hz. In this regard, there is a method according to any of the methods detailed herein and/or variations thereof, which includes method actions that entails generating mechanical vibrations using a bone conduction system based on inputs into a sound capture system of the bone conduction system (this can be executed when executing method action 1220 above). The mechanical vibrations include vibrations below about 2000 Hz (e.g., 200 Hz, 300 Hz, 400 Hz, 500 Hz, 600 Hz, 700 Hz, 800 Hz, 900 Hz, 1000 Hz, 1100 Hz 1200 Hz, 1300 Hz, 1400 Hz, 1500 Hz, 1600 Hz, 1700 Hz, 1800 Hz, 1900 Hz, or 2000 Hz, or any value or range of values therebetween in 1 Hz increments) and above about 2000 Hz (e.g., 2500 Hz or more, 3000 Hz or more, 3500 Hz or more, 4000 Hz or more, 4500 Hz vibrating the actuator or more, 5000 Hz or more, 5500 Hz or more, 6000 Hz or more, 6500 Hz or more, 7000 Hz or more, 7500 Hz or more, 8000 Hz or more, 8500 Hz or more, 9000 Hz or more or any value or range of values therebetween in about 1 Hz increments), based on respective inputs of the sound capture system. The generated mechanical vibrations generated at above 2000 Hz (and/or any of the above aforementioned values thereabove) are generated so as to have an amplitude for a respective amplitude of a respective input into the sound capture system that is at least about the same as, or lower than the generated mechanical vibrations generated below 2000 Hz (and/or any of the above aforementioned values thereabove) for a respective amplitude of a respective input of the sound capture system.

In view of the above, an exemplary embodiment entails vibrating actuator at frequencies above 2000 Hz but not amplifying the output thereof to account for the attenuation that occurs for these frequencies with respect to the tissue of the recipient (e.g., the aforementioned 50$^{th}$ percentile recipient) located between the external component implantable component.

It is noted that any method detailed herein also corresponds to a disclosure of a device and/or system configured to execute one or more or all of the method actions associated therewith, detailed herein. In an exemplary embodiment, this device and/or system is configured to execute one or more or all of the method actions in an automated fashion. That said, in an alternate embodiment, the device and/or system is configured to execute one or more or all of the method actions after being prompted by a human being. It is further noted that any disclosure of a device and/or system detailed herein corresponds to a method of making and/or using that the device and/or system, including a method of using that device according to the functionality detailed herein.

It is further noted that any disclosure of a device and/or system detailed herein also corresponds to a disclosure of otherwise providing that device and/or system and a disclosure of a method of using that system.

While various embodiments of the present invention have been described above, it should be understood that they have been presented by way of example. It will be apparent to persons skilled in the relevant art that various changes in form and detail can be made therein without departing from the spirit and scope of the invention.

What is claimed is:

1. A transcutaneous radio frequency (RF) communication system, comprising:
   an external component including:
     a first RF communication apparatus;
     a transducer configured to at least one of convert electrical input into mechanical output or convert mechanical input into electrical output; and
     a first magnetic apparatus; and
   an implantable component including:
     a second RF communication apparatus; and
     a second magnetic apparatus, wherein
   the system is configured to hold the external component to skin of a recipient of the implantable component the recipient via magnetic attraction between the first magnetic apparatus and the second magnetic apparatus with a force of between and including about 0.75N to about 1.05N when the first magnetic apparatus is separated from the second magnetic apparatus by about 1 mm to about 10 mm of human skin.

2. The system of claim 1, wherein:
   the first magnetic apparatus is a neodymium magnet having a magnetic field strength of between about 900 mT to about 1600 mT.

3. The system of claim 1, wherein:
   an input/output path of the transducer is at least approximately concentric with the first magnetic apparatus; and
   the first RF communication apparatus includes a first RF coil that extends about the first magnetic apparatus and is at least approximately concentric with the first magnetic apparatus.

4. The system of claim 1, wherein:
   the transducer is an actuator of a bone conduction device.

5. The system of claim 1, wherein:
   the external component is configured to vibrate, thereby evoking a hearing percept.

6. The system of claim 1, wherein:
   the implantable component further comprises a receiver/stimulator of a cochlear implant, of which the second RF communication apparatus is apart, wherein the receiver/stimulator is configured to use signals received by the second RF communication apparatus generated by the first RF communication apparatus as a basis upon which to generate an electrical current to evoke an electrical based hearing percept.

7. The system of claim 1, wherein:
the first RF communication apparatus includes a first RF coil that is concentric with the first magnetic apparatus;
the second RF communication apparatus includes a second RF coil that is concentric with the second magnetic apparatus; and
the system is configured such that an input/output path of the transducer is at least approximately concentric with the first magnetic apparatus and the second magnetic apparatus, and the first RF coil is at least approximately concentric with the second RF coil when the external component is adhered to the recipient via the magnetic attraction.

8. The system of claim 1, wherein:
the external component is a button sound processor including a sound processor and the transducer.

9. A method, comprising:
evoking a first hearing percept in a recipient via electrical stimulation of a first cochlea thereof based on a transcutaneous transmitted RF signal; and
evoking a second hearing percept in the recipient via bone conduction stimulation of the first cochlea based on a transcutaneously transmitted mechanical vibration, wherein
the transcutaneously transmitted mechanical vibration and the transcutaneously transmitted RF signal enter the skin of the recipient at least at locations that are proximate one another.

10. The method of claim 9, wherein:
the transcutaneously transmitted mechanical vibration and the transcutaneously transmitted RF signal enter the skin of the recipient at the same location.

11. The method of claim 9, wherein:
the transcutaneously transmitted RF signal is generated by an inductance field, and
the transcutaneously transmitted mechanical vibration enters the skin of the recipient at a location that is at least approximately concentric with the generated inductance field.

12. The method of claim 9, wherein:
the recipient includes a second cochlea, and the transcutaneously transmitted mechanical vibration and the transcutaneously transmitted RF signal enter the skin of the recipient at locations closer to the first cochlea than to the second cochlea.

13. The method of claim 9, wherein:
the recipient includes a second cochlea, and the transcutaneously transmitted mechanical vibration and the transcutaneously transmitted RF signal enter the skin of the recipient at locations closer to the second cochlea than to the first cochlea.

14. The method of claim 9, wherein:
the transcutaneously transmitted mechanical vibration is no higher than about 2000 Hz.

15. The method of claim 9, further comprising:
generating the transcutaneously transmitted mechanical vibration using a bone conduction system based on inputs into a sound capture system of the bone conduction system, wherein
the mechanical vibration includes mechanical vibrations below about 2000 Hz and above about 2000 Hz, based on respective inputs of the sound capture system, and
the mechanical vibrations generated at above about 2000 Hz are generated so as to have an amplitude for a respective amplitude of a respective input into the sound capture system that is at least about the same as or lower than the mechanical vibrations generated below about 2000 Hz for a respective amplitude of a respective input of the sound capture system.

16. The method of claim 9, further comprising:
generating the transcutaneously transmitted mechanical vibration using a bone conduction system based on inputs into a sound capture system of the bone conduction system, wherein
the mechanical vibration includes vibrations below about 2000 Hz and above about 2000 Hz, based on respective inputs of the sound capture system, and
the bone conduction system is configured such that the mechanical vibrations generated at above about 2000 Hz are generated so as to have an amplitude for a respective amplitude of a respective input into the sound capture system that is at least about the same as or lower than the mechanical vibrations generated below about 2000 Hz for a respective amplitude of a respective input of the sound capture system.

17. A device, comprising:
an inductive radio frequency (RF) communication coil; and
a platform apparatus configured to at least one of be secured to or be coupled to an apparatus comprising an actuator so as to establish a vibrational path, when the platform apparatus is secured and/or coupled to the apparatus comprising the actuator, from the apparatus comprising the actuator to a skin interface portion of the platform apparatus, wherein
the coil is proximate the skin interface portion.

18. The device of claim 17, further comprising:
the actuator, wherein the actuator is complexly mechanically secured to the platform apparatus.

19. The device of claim 17, further comprising:
the apparatus comprising the actuator, wherein the apparatus comprising the actuator is simply mechanically coupled to the platform apparatus; and
the apparatus comprising the actuator is removably coupled to the platform apparatus.

20. The device of claim 17, wherein:
the platform apparatus includes a magnet configured to adhere the device to skin of a recipient via a magnetic attraction with an implanted magnet.

21. The device of claim 17, wherein:
the device is configured to generate vibrations to evoke a bone conduction hearing percept at the same time that an inductive RF data signal is outputted from the coil.

22. The device of claim 17, further comprising:
the device comprising the actuator, wherein the device is configured such that the platform apparatus is configured to vibrate to evoke a bone conduction hearing percept via transfer of vibrations from the platform apparatus to skin of a recipient.

23. The device of claim 17, wherein:
the device includes a bone conduction system including the apparatus comprising the actuator, wherein the apparatus comprising the actuator is configured to generate mechanical vibrations based on respective inputs into a sound capture system of the bone conduction system;
the bone conduction system is configured such that the apparatus comprising the actuator generates vibrations at below about 2000 Hz and above about 2000 Hz, based on respective inputs of the sound capture system; and the bone conduction system is configured such that the generated mechanical vibrations generated at above about 2000 Hz are generated so as to have an amplitude for a respective amplitude of the respective input into the sound capture system that is at least about the same as or lower than that of the generated mechanical vibrations generated below about 2000 Hz for a respective amplitude of the respective input of the sound capture system.

24. The device of claim 17, wherein:
the coil is separate from the platform apparatus.

25. The device of claim 17, wherein:
the coil is part of the platform apparatus.

26. The device of claim 17, wherein:
the platform apparatus is part of a button sound processor.

27. The device of claim 17, wherein:
the skin interface portion has a closed at least substantially curved outer profile with respect to a plane normal to a skin interface surface of the skin interface portion.

28. The device of claim 17, wherein:
the platform apparatus is a component configured to interface with skin of a recipient at a location away from an ear of the recipient.

29. The device of claim 17, wherein:
the securing or coupling results in material of the platform apparatus being in direct contact with the apparatus comprising the actuator.

30. A method, comprising:
generating RF signals extracutaneously to a recipient and evoking a first hearing percept in the recipient via electrical stimulation based on the RF signals; and
generating mechanical vibration signals extracutaneously to the recipient and evoking a second hearing percept in the recipient via bone conduction based on the mechanical vibration signals, wherein
the method is executed by limiting the generated vibrations to about 2000 Hz and below.

31. The method of claim 30, wherein:
the RF signals are generated using an RF inductance coil;
the mechanical vibration signals are generated using an actuator; and
the RF inductance coil and the actuator are adhered to the recipient via a same magnet system.

32. The method of claim 30, wherein:
the RF signals are generated using an RF inductance coil;
the mechanical vibration signals are generated using an actuator; and
the RF inductance coil and the actuator are integrated into a button sound processor.

33. The method of claim 30, wherein:
the mechanical vibration signals are generated using a bone conduction system, wherein the bone conduction system is limited to generating vibrations of about 2000 Hz and below by at least one of structure, circuitry or programming.

* * * * *